(12) United States Patent
Cotton et al.

(10) Patent No.: US 6,707,542 B1
(45) Date of Patent: *Mar. 16, 2004

(54) REFRACTOMETER FOR MONITORING WATER CONTENT IN FLUIDS

(75) Inventors: Christopher T. Cotton, Honeoye Falls, NY (US); Jeffrey M. Sabin, Lewiston, NY (US); Thomas E. Ryan, Batavia, NY (US)

(73) Assignee: Reichert, Inc., Depew, NY (US)

( * ) Notice: Subject to any disclaimer, the term of this patent is extended or adjusted under 35 U.S.C. 154(b) by 420 days.

This patent is subject to a terminal disclaimer.

(21) Appl. No.: 09/676,836

(22) Filed: Sep. 29, 2000

Related U.S. Application Data

(63) Continuation-in-part of application No. PCT/US00/02304, filed on Jan. 28, 2000.

(51) Int. Cl.⁷ .................................................. G01N 21/41
(52) U.S. Cl. ...................................................... 356/136
(58) Field of Search .......................... 356/128, 135–137

(56) References Cited

U.S. PATENT DOCUMENTS

| | | | | |
|---|---|---|---|---|
| 3,329,060 A | * | 7/1967 | Holleran | 356/135 |
| 4,451,147 A | * | 5/1984 | Dobes et al. | 356/135 |
| 5,243,321 A | * | 9/1993 | Iwata | 340/146.2 |
| 5,355,211 A | * | 10/1994 | Thompson et al. | 356/135 |
| 5,969,808 A | * | 10/1999 | Cotton et al. | 356/135 |
| 6,034,762 A | * | 3/2000 | Cotton et al. | 356/135 |

* cited by examiner

*Primary Examiner*—Russell Adams
*Assistant Examiner*—Michelle Nguyen
(74) *Attorney, Agent, or Firm*—Hodgson Russ LLP

(57) ABSTRACT

A refractometric apparatus and method for monitoring the percentage of water in hydraulic and non-hydraulic fluids employ a temperature sensitive device allowing a user to obtain accurate and correct readings of various measured properties. In particular, the temperature sensitive member comprises a prism-wedge-mirror combination in conjunction with a bimetallic strip. The combination ensures the proper angular displacement of a light beam inside the refractometric apparatus and, therefore, the correct reading of a parameter to be measured.

17 Claims, 26 Drawing Sheets

| DOT 3, N=7 | | | |
|---|---|---|---|
| | BOILING POINT | PERCENT H$_2$O (WT./WT.) | REFRACTIVE INDEX, nD |
| FRESH BOILING POINT | 252 C. +/- 7 C. | 0.23 +/- 0.14 | 1.4435 +/- 0.0004 |
| RANGE | 240-262 C. | 0.06-0.42 | 1.4428-1.4440 |
| MIN. DRY BOILING POINT | 250 C. | 1.15 +/- 0.38 | 1.4429 +/- 0.0004 |
| RANGE | | | |
| MIN. WET BOILING POINT | 140 C. | 4.4 +/- 0.3 | 1.4406 +/- 0.0004 |
| RANGE | | | |
| HIGH TEMP DOT 3, N = 6 | | | |
| FRESH BOILING POINT | 281 C. +/- 18 C. | 0.14 +/- 0.07 | 1.4457 +/- 0.0004 |
| RANGE | 263-305 C. | 0.07-.26 | 1.4449-1.4460 |
| MIN. DRY BOILING POINT | 205 C. | 1.56 +/- 0.35 | 1.4447 +/- 0.0004 |
| MIN. WET BOILING POINT | 140 C. | 4.65 +/- 0.39 | 1.4425 +/- 0.0004 |
| DOT 4, N = 9 | | | |
| FRESH BOILING POINT | 259 C. +/- 18 C. | 0.18 +/- 0.08 | 1.4452 +/- 0.0005 |
| RANGE | 248-264 C. | 0.06-0.30 | 1.4448-1.4462 |
| MIN. DRY BOILING POINT | 230 C. | 1.11 +/- 0.28 | 1.4447 +/- 0.0005 |
| MIN. WET BOILING POINT | 155 C. | 5.1 +/- 0.46 | 1.4418 +/- 0.0005 |

FIG.3

| WATER CONCENTRATION PERCENT (WEIGHT/WEIGHT) | DOT 3 N = 9 | DOT 4 N = 7 |
|---|---|---|
| NEW | −0.00038 +/− 0.00002 | −0.00041 +/− 0.00004 |
| 2% | −0.00038 +/− 0.00003 | −0.00040 +/− 0.00004 |
| 4% | −0.00039 +/− 0.00002 | −0.00039 +/− 0.00003 |
| 6% | −0.00037 +/− 0.00003 | −0.00038 +/− 0.00002 |
| USED FLUID, N = 101 | −0.00037 +/− 0.000014 | |

FIG. 5

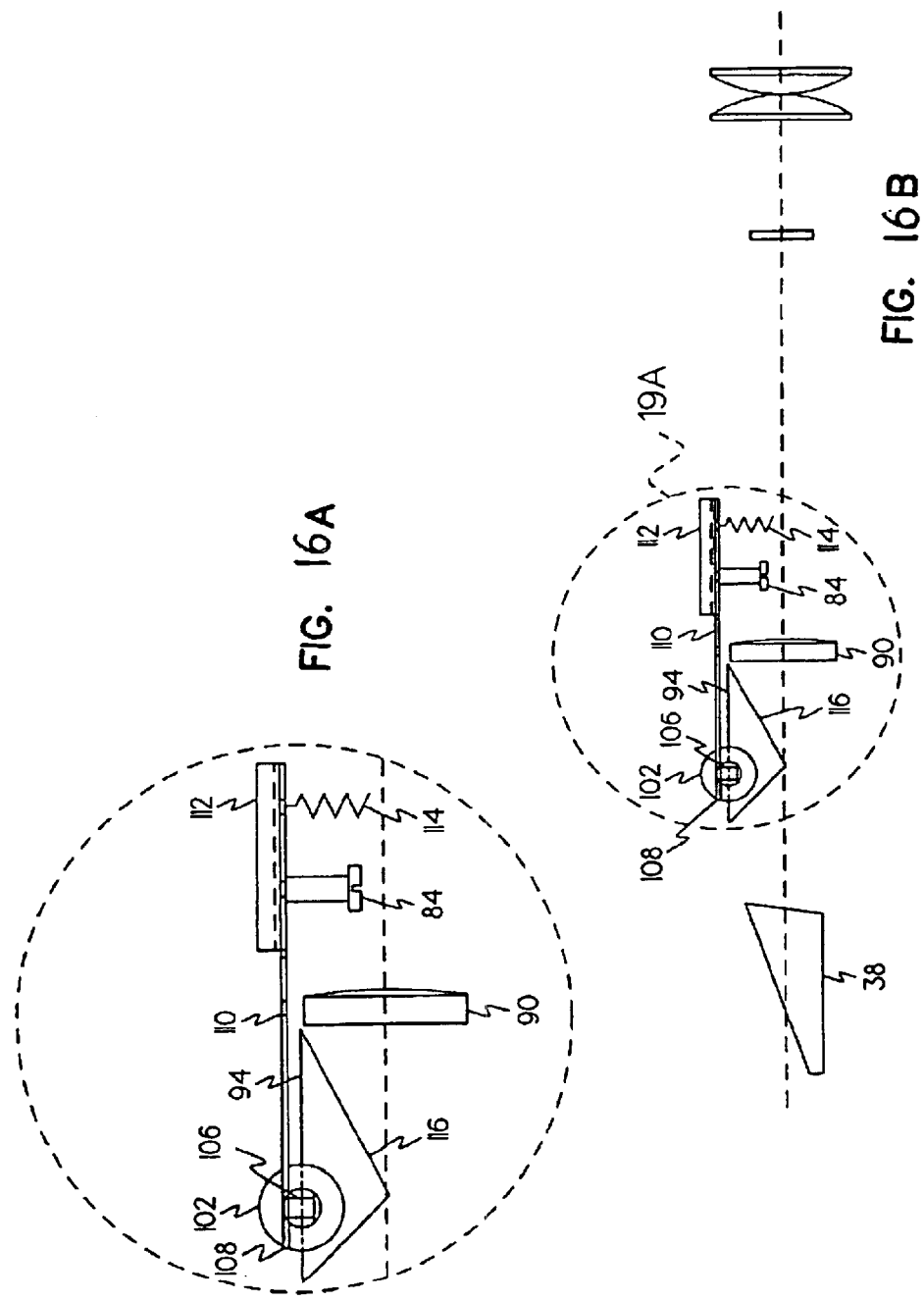

REFRACTOMETER FOR MONITORING WATER CONTENT IN FLUIDS

CROSS-REFERENCE TO A RELATED APPLICATION

This application is a continuation-in-part of an earlier filed international patent application No. PCT/US00/02304, filed on Jan. 28, 2000, which is incorporated herein by reference.

BACKGROUND OF THE INVENTION

Monitoring the water content in hydraulic brake fluids is known to be of crucial importance in maintaining efficient and effective braking function. During the braking, especially the sustained braking, friction-generated heat can cause a brake fluid to boil and form vapor bubbles that can cause a complete loss of the braking function. Since most of the commercially used brake fluids are highly hygroscopic, the water content in such a fluid can increase due to water absorption from the surrounding environment. If the water content in a brake fluid increases to 2%, the boiling point of the fluid decreases significantly, thus, decreasing the efficiency of the brakes and overall safety of the operating device.

Another area of concern related to the high water content in brake fluids is the increase of the fluid's corrosive activity that can cause corrosion of the braking system components that come in contact with the brake fluid. Antilock braking systems (ABS) that are presently installed on many motor vehicles are especially susceptible to corrosion. Having water in a brake fluid during the period of about 2 years irreparably damages an ABS unit. A replacement for an ABS unit presently costs about $1,800.

Two methods of measuring water content in a brake fluid are employed in the products currently available on the market. The Karl Fisher titration method is used in a complicated device that costs around $7,000. Another type of a device that uses the method of measuring the boiling point of a brake fluid costs about $1,000. It is obvious that the majority of service stations will not be able to afford and use expensive measuring devices. Yet another method of determining water content in brake fluids by measuring conductivity of a fluid has proven to be inaccurate. Therefore, it is highly desirable to have a quick, easy and inexpensive method and device for determining water content in a brake fluid. Such method and device would allow service technicians to measure water contents in brake fluids and recommend brake fluid changes before either safety or corrosion concerns arise.

Refractometers have long been used as field instruments for a variety of applications. They have been useful in determining sugar content in grape juices, water content in honey, the concentration of water soluble metalworking lubricants and protein levels in blood serum. American Society of Testing and Materials Standard Practice D 3321 details use of a refractometer for determining the freeze point of engine coolants with far greater accuracy than traditional hydrometer methods. Refractometers require a very small sample size. Refractive index measurements are quick and can be performed with simple, relatively inexpensive instruments. Therefore, refractometry can be used to determine a percentage of water in fluids by measuring the critical angle of total reflection in a particular fluid while providing for temperature compensation that becomes necessary due to the temperature dependence of the refractive indices. Since the refractive index n of a fluid changes as the water content increases, fluids with different water contents will have different refractive indices, and, therefore, different critical angles of total reflection. Due to the phenomenon of total reflection there will be a boundary between the dark and light portions of a scale in the observation area. The location of the boundary on the scale than is calibrated in water content units will indicate the percentage of water in a tested sample of a fluid.

Refractometers that use the critical angle of total reflection to determine percentages of water in such substances as antifreeze coolants have been known in the industry. For example, U.S. Pat. No. 5,355,211 to Thompson et al. (assigned to Leica, Inc.) discloses a refractometer subassembly method and apparatus comprising critical angle prism 214 and compensating wedge 232 disposed within housing 210, as shown in FIG. 5 of that patent. Wedge 232 is attached to one end of temperature responsive member 234.

U.S. Pat. No. 4,243,321 "Handy Refractometer" to Okuda et al. discloses a handheld refractometer, as particularly illustrated in FIGS. 1 and 5 of that patent. The patent discloses mirror 12, one end of which is secured to holding member 14 for prism 3 by plate spring 13. The other end of mirror 12 is urged against thermally expansible member 15 by the force of spring 13. As temperature changes, the thermally expansible member expands or contracts, thereby rotating the mirror 12. In the Okuda patent rotation of mirror 12 about the pivot P keeps beam 53 parallel to original beam 52 in order to compensate for a temperature change.

U.S. Pat. No. 4,451,147 "Refractometer" to Dobes et al. discloses a refractometer that utilizes light refracting wedge 40, mirror 18, mirror surface areas 32 and 44, and prism 22, as illustrated in FIGS. 1, 2 and 3 of that patent. According to the Dobes patent, mirror 18 reflects beam 54 and directs it to prism 22. At the lower side of prism 22 the beam splits into reference light beam 56 and measuring light beam 58. Reference light beam 56 is then reflected by mirror surface 32 of prismatic body 42 and by partial mirror surface area 44 of light refracting wedge 40. Measuring light beam 58 gets refracted at active surface area 34, and passes through light refracting glass wedge 40 to be reflected by a mirror surface at the lower side 60 of wedge 40. Temperature compensation in that patent is achieved by directing both reference and measuring beams through the same prism, thus, exposing the two beams to the same temperature differences. For the Dobes invention to operate prism 22 has to be partially coated with a reflective coating.

Due to the nature of certain chemicals contained in brake fluids, there are two problems that are specific to brake fluids and that render the known refractometers completely inapplicable to measuring refractive properties of such fluids.

First, the range of the refractive index n in a brake fluid spans from about 1.4447 at 0% of water to about 1.4394 at 7% of water. This range is much narrower than that of a coolant (spanning from about 1.33 to about 1.38 over the same range of the percentages of water). Thus, a much more sensitive device reflecting a different refractive index range is necessary to design a brake fluid refractometer. The increased sensitivity requirement can be satisfied by achieving more accurate temperature compensation. The known method of temperature compensation employed in a refractometer for coolants uses a bimetallic strip attached to a temperature compensating prism (called "a wedge" in the following description of the present invention) and to the prism on which a sample fluid is deposited. The material of the compensating prism is such that its temperature coefficient (dn/dT) is negative if the temperature coefficient of the sample fluid is positive, and vice versa. The bimetallic strip deflects from its initial position when temperature changes, changing the angle of the attached compensating prism and, thus, providing for the correct temperature compensation in measuring the refractive index of a sample fluid.

The concept of using two materials with opposite temperature coefficients and a bimetallic strip has been known and used in the industry. It is described, for example, in U.S. Pat. No. 3,329,060 to Holleran and U.S. Pat. No. 3,267,795 to Goldberg which are incorporated herein by reference.

Such a design for temperature compensation proved to be unworkable in the case of measuring water contents in brake fluids. The temperature coefficient of a brake fluid is approximately 3 times smaller than the temperature coefficient of a coolant ($-38 \times (10)^{-5}$/° C. for a brake fluid, $-12 \times (10)^{-5}$/° C. for a coolant). Therefore, a much more sensitive temperature compensation device is needed to measure water content in a brake fluid over a temperature range typical for a regular service station. Because of the increased sensitivity requirements a bimetallic strip used in the refractometer for coolants can not provide the necessary angular compensation. Therefore, a new temperature compensation device is needed for a brake fluid refractometer.

A second problem arises from the fact that in a brake fluid the refractive index changes negatively with the increase of the water content, whereas, for example, in a coolant the refractive index increases with the increase of glycol. Thus, there exists a need of inverting the image on the reading scale so that the bottom of the scale will correspond to 0% of water and the top of the scale will correspond to 7% of water in a brake fluid. Such inversion is highly desirable because the bottom-to-top calibration is familiar to the customers and has been used in already existing coolant refractometers.

It is also greatly desirable to have a refractometric apparatus that would allow a user to determine not only the percentage of water in a particular hydraulic fluid, but also the boiling point of such a fluid. Such an apparatus would be especially useful, for example, in servicing race cars, because for servicing such cars properly it is the boiling point that needs be determined in order to prevent the loss of the braking function.

SUMMARY OF THE INVENTION

It is therefore, a primary of the present invention to provide a refractometric apparatus and method for use with a hydraulic fluid, such as brake fluid, which solves the above enumerated problems. The present invention provides a refractometric apparatus and method employing a temperature sensitive member that provides correct readings of the water content and a boiling point on the reticle. In particular, the temperature sensitive member comprises a prism-wedge-mirror combination in conjunction with a bimetallic strip.

In a particular embodiment of the present invention the use of a mirror achieves the increased angular deviation of the beam. Changing the position of the mirror changes the angular deviation of the beam in ratio 2 to 1. Therefore, a more sensitive temperature compensation in a brake fluid refractometer is achieved by introducing a mirror between the prism with a sample of a hydraulic fluid and the wedge. In a coolant refractometer, the old temperature compensation combination without a mirror lead to an angular displacement of the beam of only a fraction of 1° when a wedge rotated 1°.

It is another object of the present invention to stretch a narrower range of brake fluid refractive indices over a larger scale than is normally used in refractometers for coolants. A larger angular displacement carried over the distance between the focusing lens and the reticle will provide a larger span of an image on the scale of the reticle.

It is yet another object of the present invention to achieve image inversion in a refractometer for brake fluids. The portion of the beam that previously got totally reflected on the boundary between the sample fluid and the prism and the portion of the beam that did not get totally reflected change places after the beam is reflected by the mirror, thus, inverting the image that a user will subsequently see on the scale.

And yet another object of the present invention is to incorporate a novel reticle into a hydraulic fluid refractometer. The new reticle comprises one or more scales that indicate, for example, the percentage of water in and the boiling point of a particular hydraulic fluid.

And another object of the present invention is to provide a kit comprising at least two refractometers for use with corresponding hydraulic fluids.

These and other objects and advantages of the present invention will become increasingly more apparent to those skilled in the art by reference to the following description and to the accompanied drawings.

BRIEF DESCRIPTION OF THE DRAWINGS

FIG. 3 is a chart including data on results obtained in determining average water concentration and refractive index from the information in FIGS. 1 and 2;

FIG. 5 is a table presenting average temperature coefficient of various brake fluids;

DETAILED DESCRIPTION OF THE PREFERRED EMBODIMENT

Figure 1A:
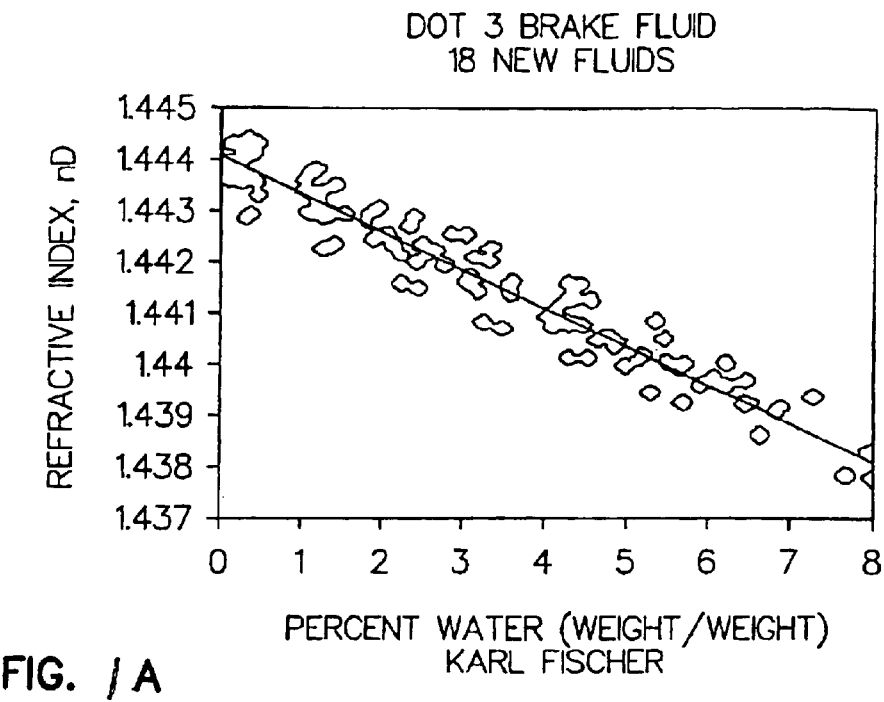
FIGS. 1A, 1B and 1C are graphs illustrating the relationship between refractive index and water content and boiling point of various brake fluids.

Brake fluids circulating in different makes of motor vehicles made and driven in countries around the world come in a wide variety of combinations of chemicals. Various makes of cars built by a particular manufacturer as well as cars of the same class built by different manufacturers require different types of brake fluids to maintain proper and reliable braking function. The variety of types of brake fluids makes the task of designing a single device for measuring certain properties of different brake fluids an especially daunting problem. Therefore, in order to design and build a refractometer that relates the refractive index n to the boiling point and a percentage of water in a population of brake fluids available on the market, it is necessary to assure that the optical properties of various brake fluids are such that the refractive indices of the fluids are still within the range that is adaptable to obtaining a clear reading on the reticle. The following tests and measurements performed on "clean" break fluids diluted with water and brake fluids taken from actual motor vehicles illustrate and support the concept of adaptability of a brake fluid refractometer of the present invention to determining water content and boiling points of different brake fluids.

EXAMPLE 1

The Range of Absolute Refractive Indices in Brake Fluids

The chart illustrating the value of absolute refractive indices of 33 new brake fluids as well as the refractive indices of the same brake fluids diluted by water up to 7% with an increment of 1% of water in most experiments, is provided in FIG. 1 of application PCT/US00/02304 and in U.S. Pat. No. 6,034,762, incorporated herein by reference. An absolute refractive index of a fluid is its refractive index at 0% of water in the fluid. In this example various brands of brake fluids were purchased at a store, then an absolute refractive index of a pure, undiluted brake fluid was measured. After that, refractive indices of diluted samples of brake fluids were determined. In all measurements the refractive indices were measured on a NIST Traceable laboratory refractometer. The percentage of water in the samples were determined by the Karl Fisher titration method that is well-known to those skilled in the art.

Brand names and types of the brake fluids and the percentages of water in these fluids are provided in Columns 1, 3 and 4. Column 8 provides refractive indices for all pure brake fluids as well as brake fluids diluted by water up to 7% at 20° C. It can be seen from Column 8 that at 20° C. the absolute values of refractive indices lie within the range between about 1.44721 for the DOT 4+ Volvo brake fluid brand and about 1.44344 for the DOT 3 Delco (GM) brand. The fact that all the absolute refractive indices fall within such a range makes that range convenient for obtaining a good reading on a reticle of the refractometer. Therefore, the above data conclusively show that it is possible to build a refractometer which is capable of providing accurate readings for a variety of different brake fluids.

EXAMPLE 2

Figure 1B:
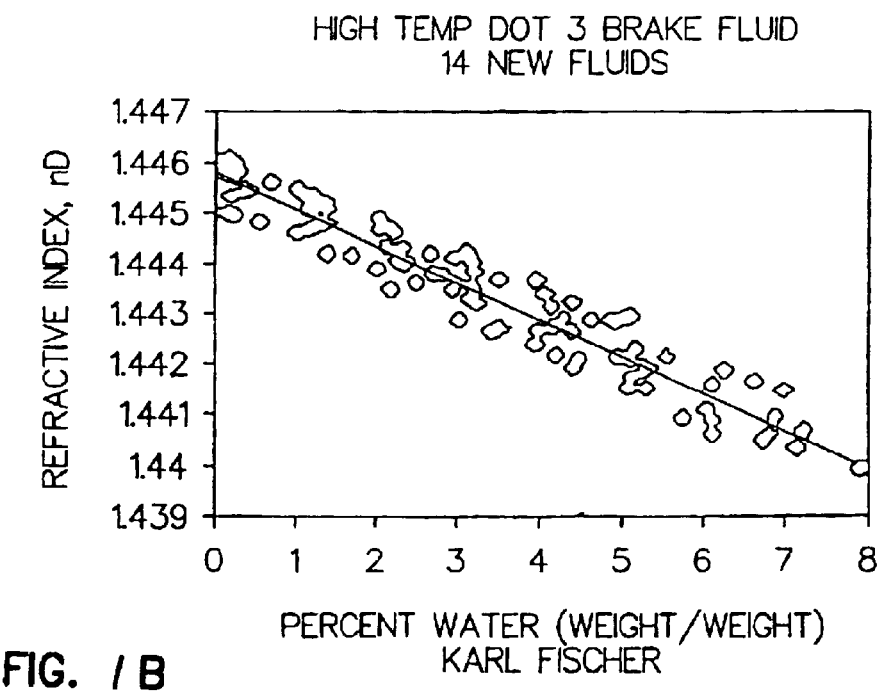
Figure 1C:
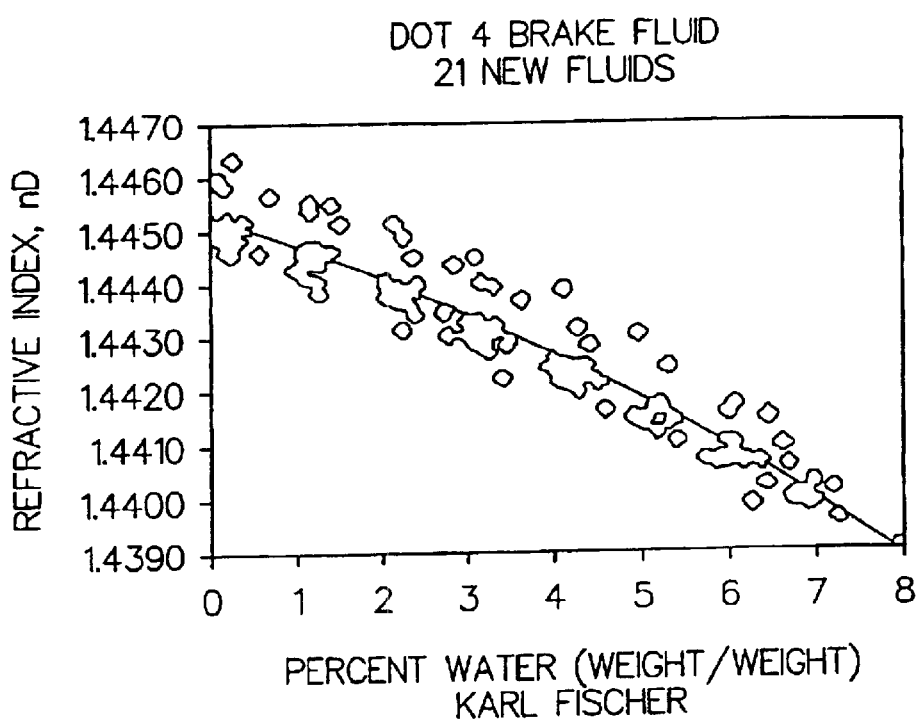

The Relationship Between Refractive Index, Water Content and Boiling Point of Brake Fluids The relationship between refractive index and water concentration for DOT 3, High Temperature DOT 3 and DOT 4 brake fluids is shown in FIGS. 1A, 1B and 1C, respectively. Water in amounts of 1% to 8% water in increments of approximately 1% was added to each new fluid to develop these data. Refractive indices were measured at approximately 20° C. and 24° C. and were corrected to 20.0° C. All three types of brake fluid exhibited excellent correlation between refractive index and water concentration despite the fact that the composition from fluid to fluid within a category may vary. The curve fitted data in FIGS. 1B and 1C are almost identical. This demonstrates that there is no appreciable difference between the refractive index and water concentration correlation for the High Temperature DOT 3 and DOT 4 fluids.

Figure 2:
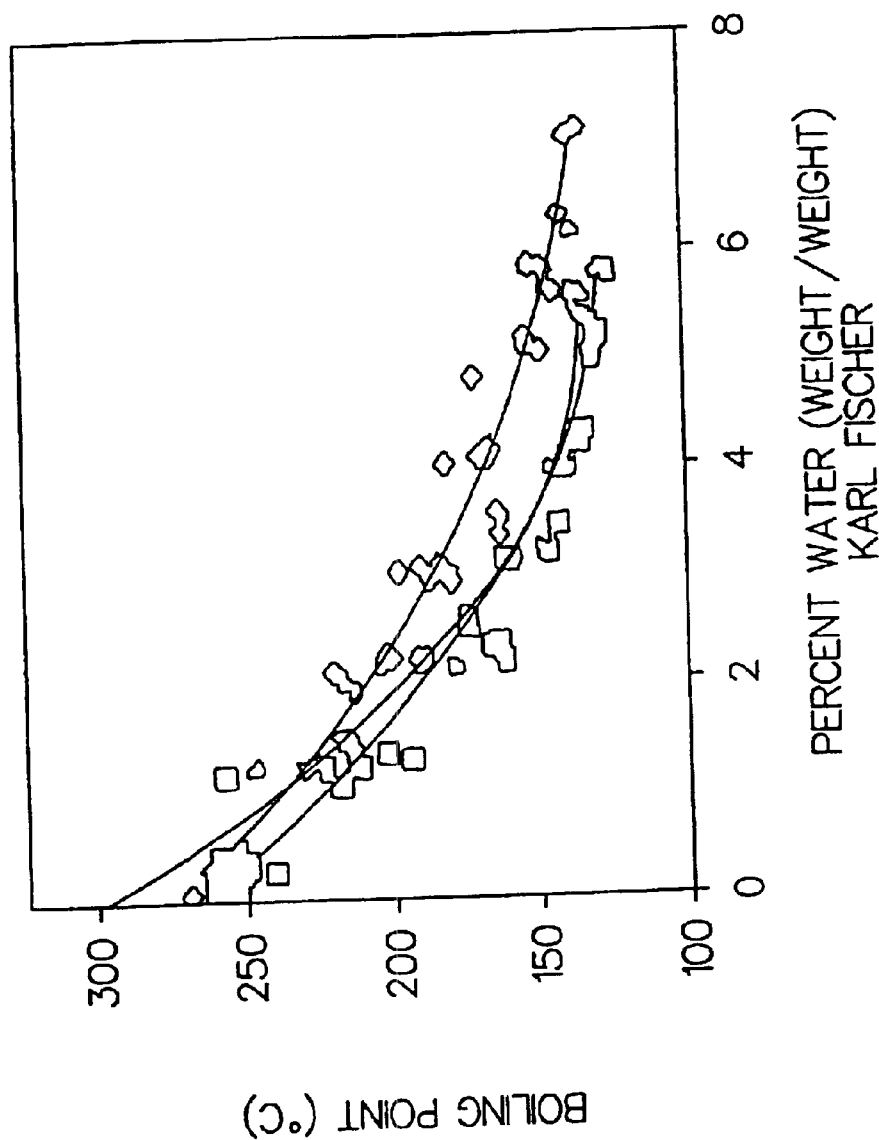
FIG. 2 is a graph illustrating the relationship between boiling point and water as determined by the Karl Fischer titration method.
Figure 4:
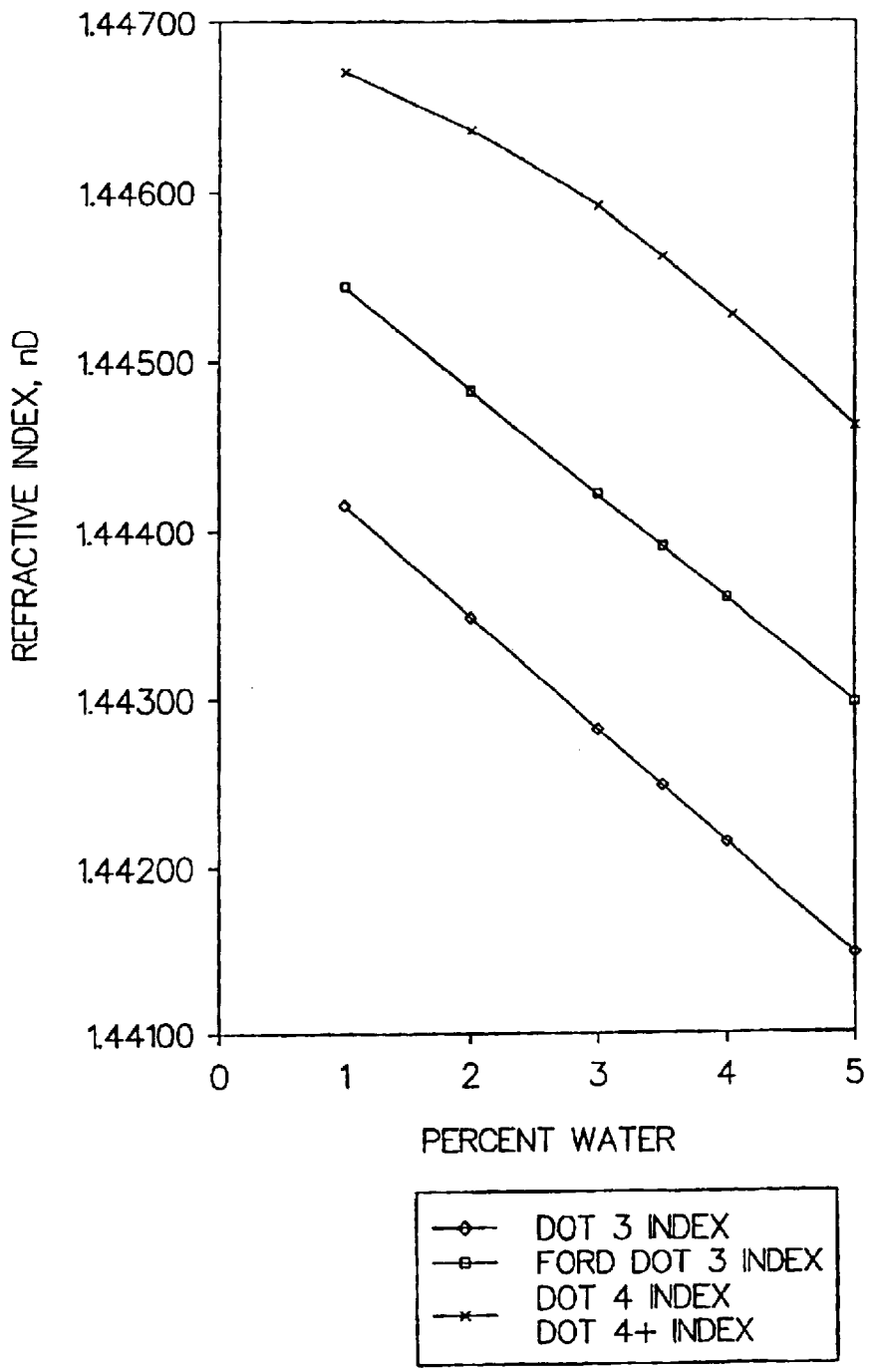
FIG. 4 is a graph illustrating dependency of refractive indices of brake fluids on percentage of water.

The boiling points of a smaller number of fluids were also determined over a 1% to 6% water concentration range. The relationship between boiling point and water content as determined by Karl Fischer titration is shown in FIG. 2. The results from FIGS. 1 and 2 were used to determine average water concentration and refractive index at the specified wet and dry boiling points for DOT 3 and DOT 4 fluids. These results are presented in the chart of FIG. 3 along with the average boiling point, % water and refractive index for fluid fresh from the container. All of the studied fluids greatly exceeded the minimum wet and dry boiling points specified by Society of Automotive Engineers J1703 and Department of Transportation Motor Vehicle Safety Standard No. 116. The dependency of the refractive indices of DOT 3, Ford DOT 3, and DOT 4+ types of brake fluids on the percentage of water is also illustrated in FIG. 4. It follows from the graph in FIG. 1 that the decrease of the refractive indices with the increase of water is generally constant in all tested brake fluids. In other words, the slope dn/d (%$H_2O$) of the curves in FIG. 1 is constant over the range from about 1% to about 5% of water.

The fact that in all of the tested brake fluids the refractive indices decrease at about the same rate makes it possible to design a brake fluid refractometer with a reticle that will provide accurate readings of water content and the boiling points for a wide variety of brake fluids available on the market.

EXAMPLE 3

Temperature Coefficient and Dispersion in Brake Fluids

Temperature has a large effect on refractive index measurements and must be controlled or corrected very carefully. Aqueous solutions generally exhibit a temperature coefficient of −0.0001 to −0.0002. The temperature coefficient of organic liquids is approximately −0.0004. Such a coefficient corresponds to about 0.5% change in concentration per degree centigrade. The temperature coefficients of new DOT 3, High Temperature DOT 3 and DOT 4, brake fluid were identical. The average temperature coefficient of a sampling of used DOT 3 brake fluid is also identical. Temperature coefficient data are shown in the chart of FIG. 5. Turning back to the chart of FIG. 1 of U.S. Pat. No. 6,034,762, incorporated herein by reference, Column 14 represents the results of the measurements of differential temperature coefficients dn/dT for all of the tested brake fluids. These coefficients fall within the range of about $-30*10^{-5}/°$ C. to $-50*10^{-5}/°$ C. The average value of the temperature coefficient was determined as $-0.000388416/°$ C. The average value of the temperature coefficient accurately reflects the changes of the refractive indices n for the tested fluids as the temperature of the environment increases or decreases. Because the temperature coefficient stays about the same, it was possible to devise a single temperature compensation system for the refractometer of the present invention. Such a system compensates for temperature changes in the refractive indices in all of the variety of brake fluids.

A related important property of brake fluids discovered and implemented in the present invention is their constant dispersion. Dispersion reflects the change of the refractive indices with respect to the wavelength of the incident beam of light, $dh/d\lambda$. If the dependence of refractive indices on the wavelength were not constant, it would be impossible to get a reading on the scale of the output device of the refractometer in the form of a sharp boundary. Dispersion would cause light of different wavelengths to be refracted at different angles, therefore, producing a multicolored boundary incapable of indicating a particular value corresponding to the refractive index.

It turned out that in the tested brake fluids the ratio $dn/d\lambda$ remained constant for different formulations of brake fluids. Therefore, the reading formed on the reticle of the refractometer was in the form of sharp boundary between light and dark areas. Such a reading is perfectly suitable for accurately representing the values of the percentages of water and boiling points of brake fluids measured by the refractometer of the present invention.

EXAMPLE 4

Similarity Between "Clean" and "Used" Brake Fluids

Measurements of water content and boiling points of different brake fluids were performed on "clean", new fluids bought in a store and later diluted with water. Obviously, in real life the new brake fluid refractometer is going to be used to determine the same parameters in "used" brake fluids, the ones removed from cars after use. It is important, therefore, to establish that the optical properties of "new" and "used" brake fluids that have the same water content are similar. If such a similarity of the reticle readings corresponding to a tested "clean" break fluid with a certain percentage of water and to a "used" brake fluid with the same percentage of water is proven, then the conclusion is that the refractometer of the present invention will show the correct readings for various brake fluids from cars in use and tested by technicians and service people at different car service establishments.

Figure 6:
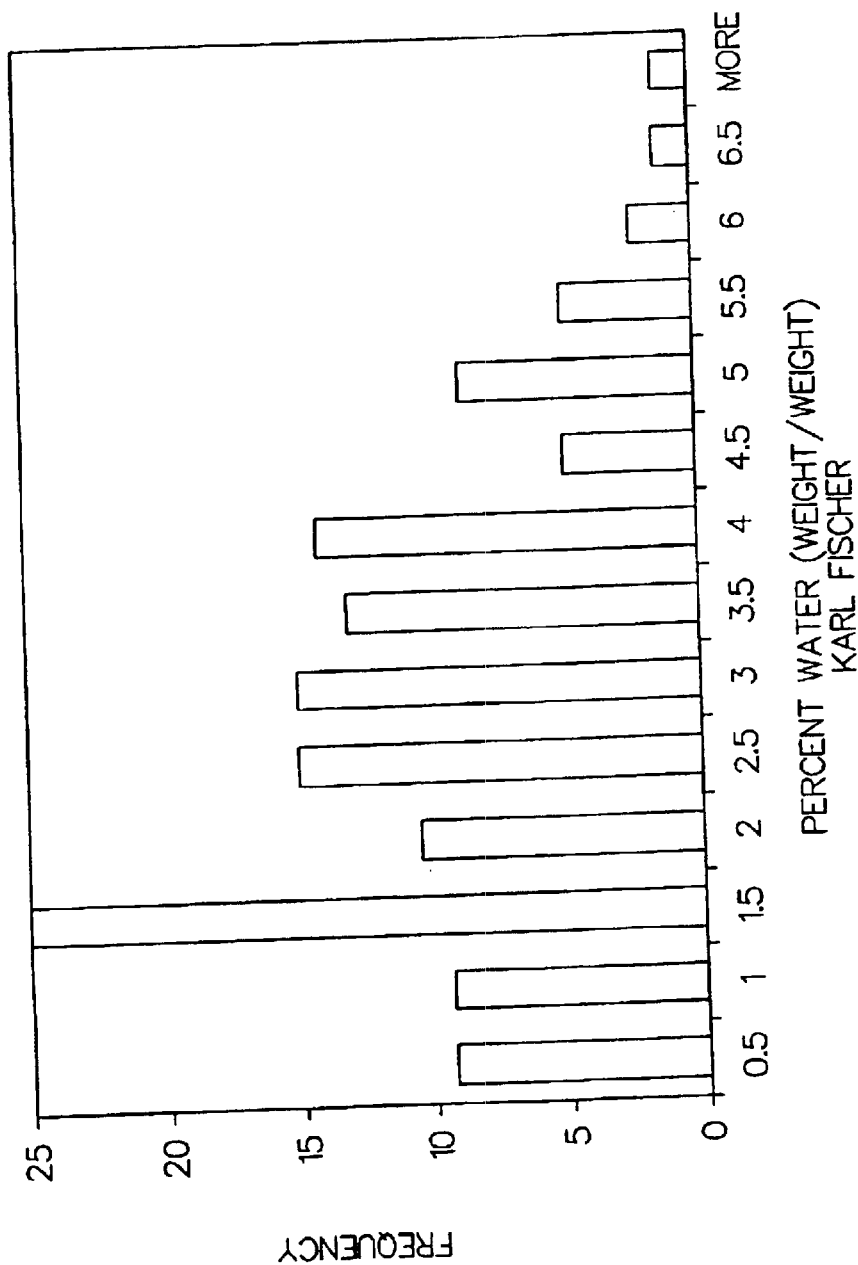
FIG. 6 is a histogram showing water content in brake fluid of various vehicles.
Figure 7:
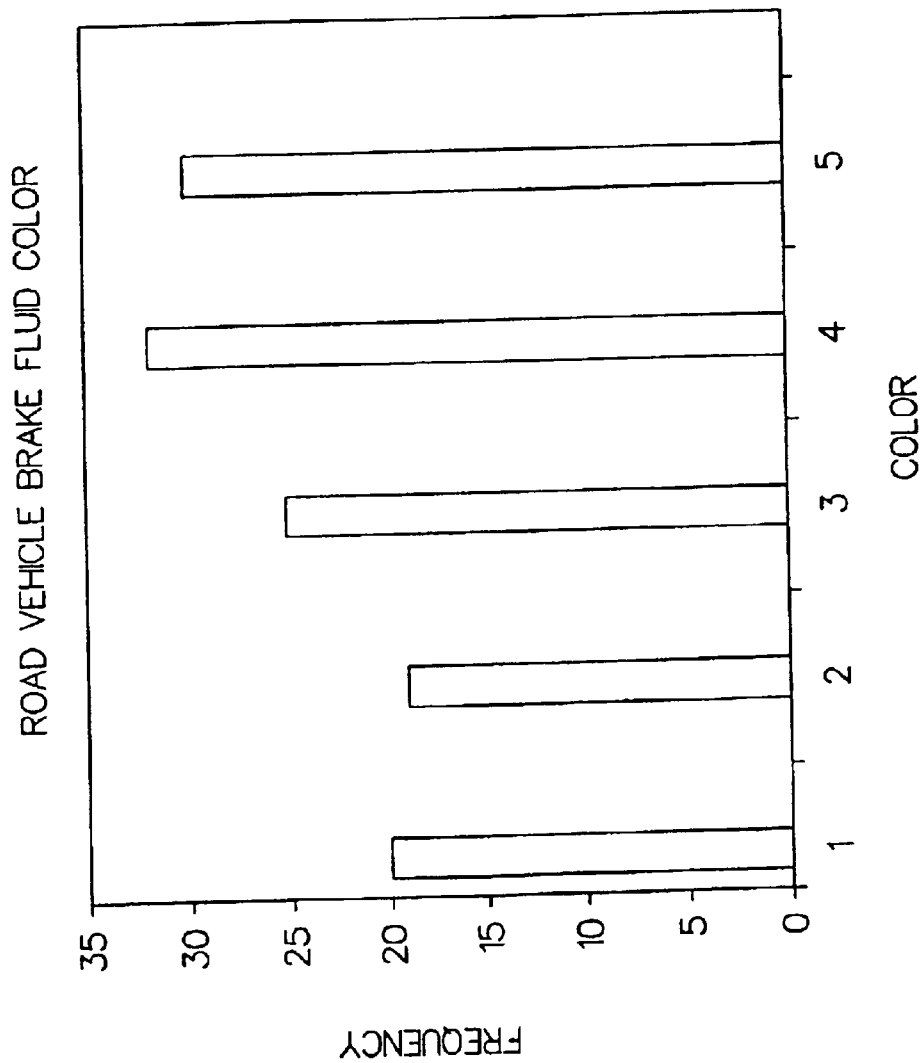
FIG. 7 is a histogram illustrating a distribution of color intensities in the samples of used brake fluids.

The chart representing the measurements of the refractive indices and temperature coefficients of "used" brake fluids, the same optical properties that were measured and presented in the chart for "clean" brake fluids is represented in FIG. 7 of U.S. Pat. No. 6,034,762, which is incorporated herein by reference. The master cylinder brake fluid water content of 131 vehicles was analyzed. The reservoir cap of all the vehicles tested recommended DOT 3 Brake fluid. A histogram of the results is shown in FIG. 6. The average water concentration in the vehicles tested was 2.6%+/− 1.5%. The vehicles ranged in year from 1976 to 1997. Average age of the vehicles was 8 years +/−4 years. The median water content was 2.4%. In 60% of the vehicles the measured water content was greater than 2%. Twenty-five percent of the vehicles had a water content greater than 4%, near the wet equilibrium reflux boiling point of typical DOT 3 brake fluid.

The physical appearance of the fluids tested varied greatly from sample to sample. There was no indication that the color or darkness of the samples contributed to any variability in the analysis. Calculated correlation coefficients for refractive index versus % water were identical even when the darkest samples were excluded.

Figure 8:
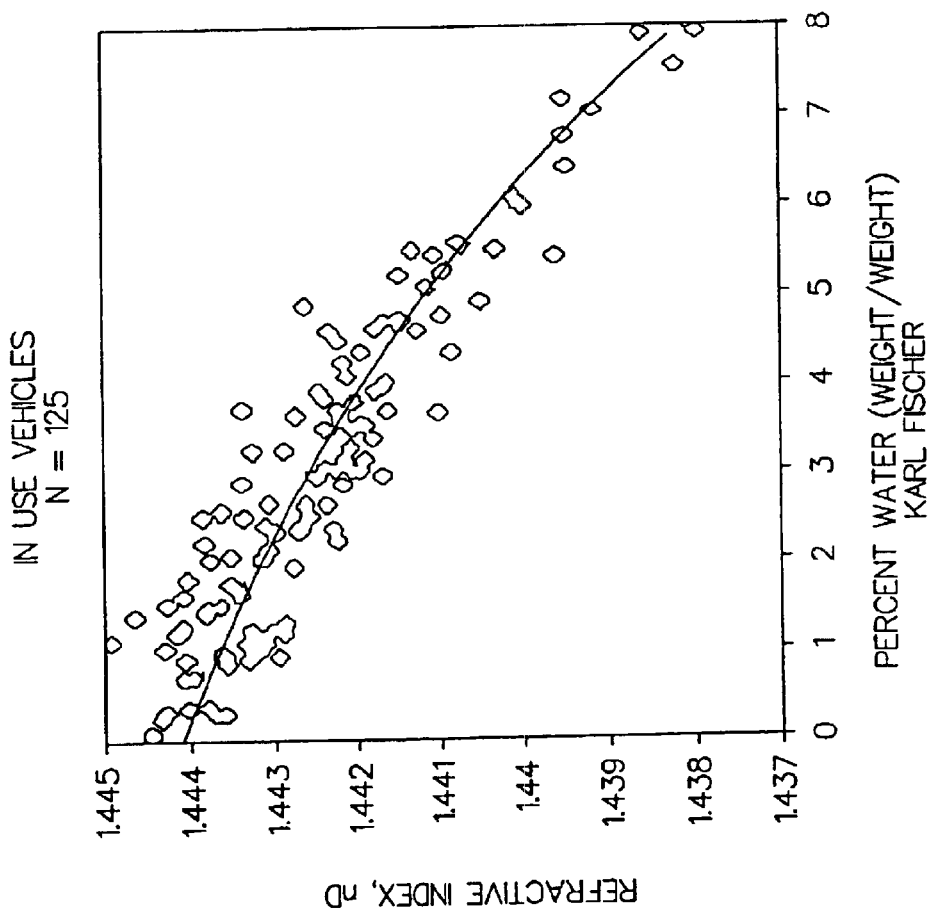
FIG. 8 is a graph comparing refractive index readings to water content for various used brake fluid samples.
Figure 9:
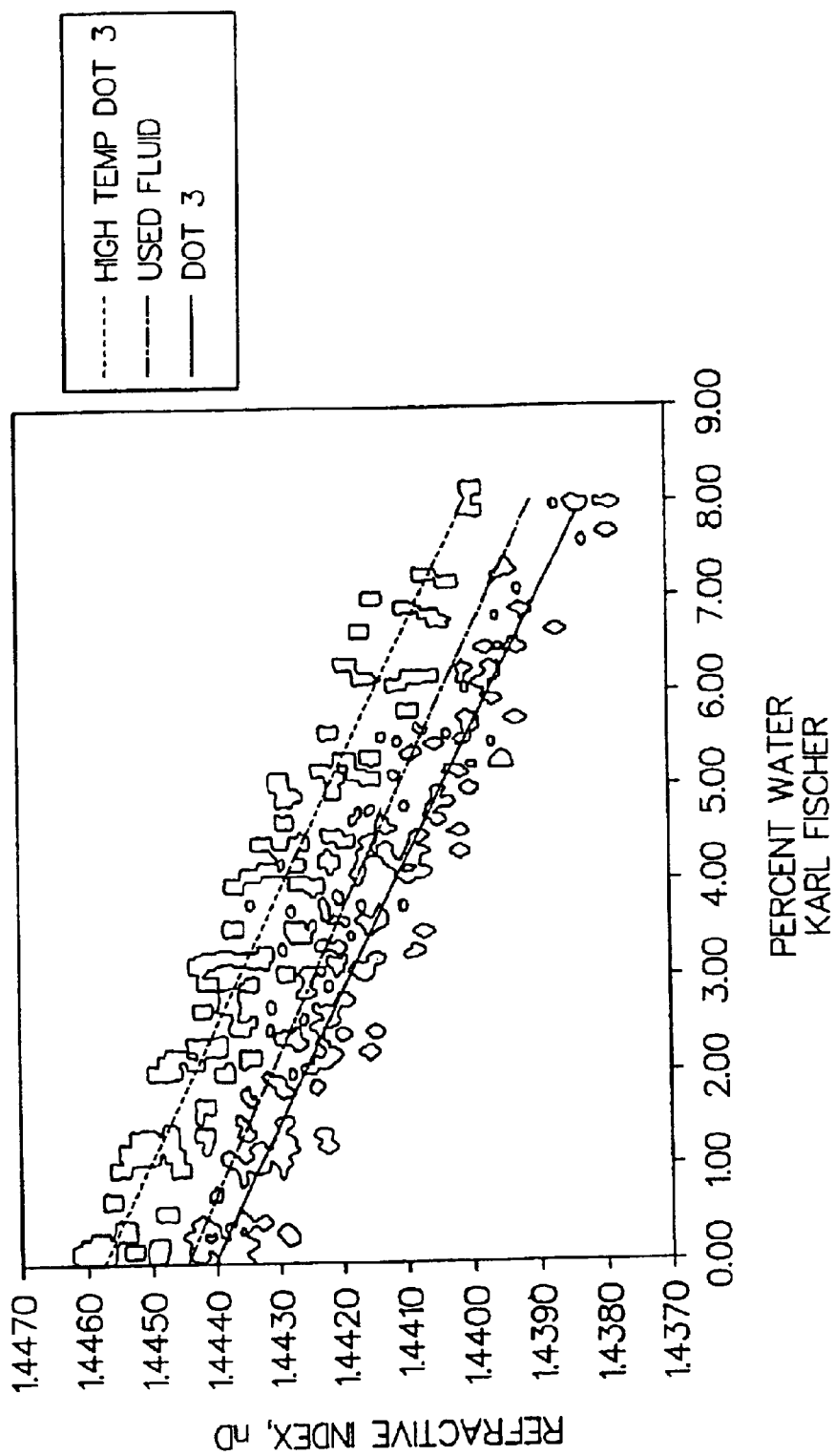
FIG. 9 is a graph comparing the data of FIG. 8 to the data of FIGS. 1A and 1B.

The data shown in FIG. 8 include all samples, regardless of color. FIG. 9 compares refractive index readings to water content for 125 "in use" road vehicles. No attempt was made to differentiate between standard DOT 3 and High Temperature DOT 3 used brake fluids. A curve for the used brake fluid data falls between the curve fit lines for clean standard DOT 3 and high temperature DOT 3 fluids as shown in FIG. 9.

The refractive indices of the "used" brake fluids fell within the range of 1.43907 to 1.44588, which is practically identical to the range of the refractive indices observed for diluted brake fluids in Example 1. Moreover, the "used" and diluted "clean" brake fluids containing the same percentage of water had approximately the same refractive indices and temperature coefficients.

Therefore, examples 1–4 show that optical properties of a wide variety of commercially available brake fluids used in different makes of cars are such that a single measuring device providing accurate readings of the percentages of water and boiling points of the brake fluids can be designed. The present invention implements the principles illustrated by examples 1–4 in a brake fluid refractometer.

Figure 10:
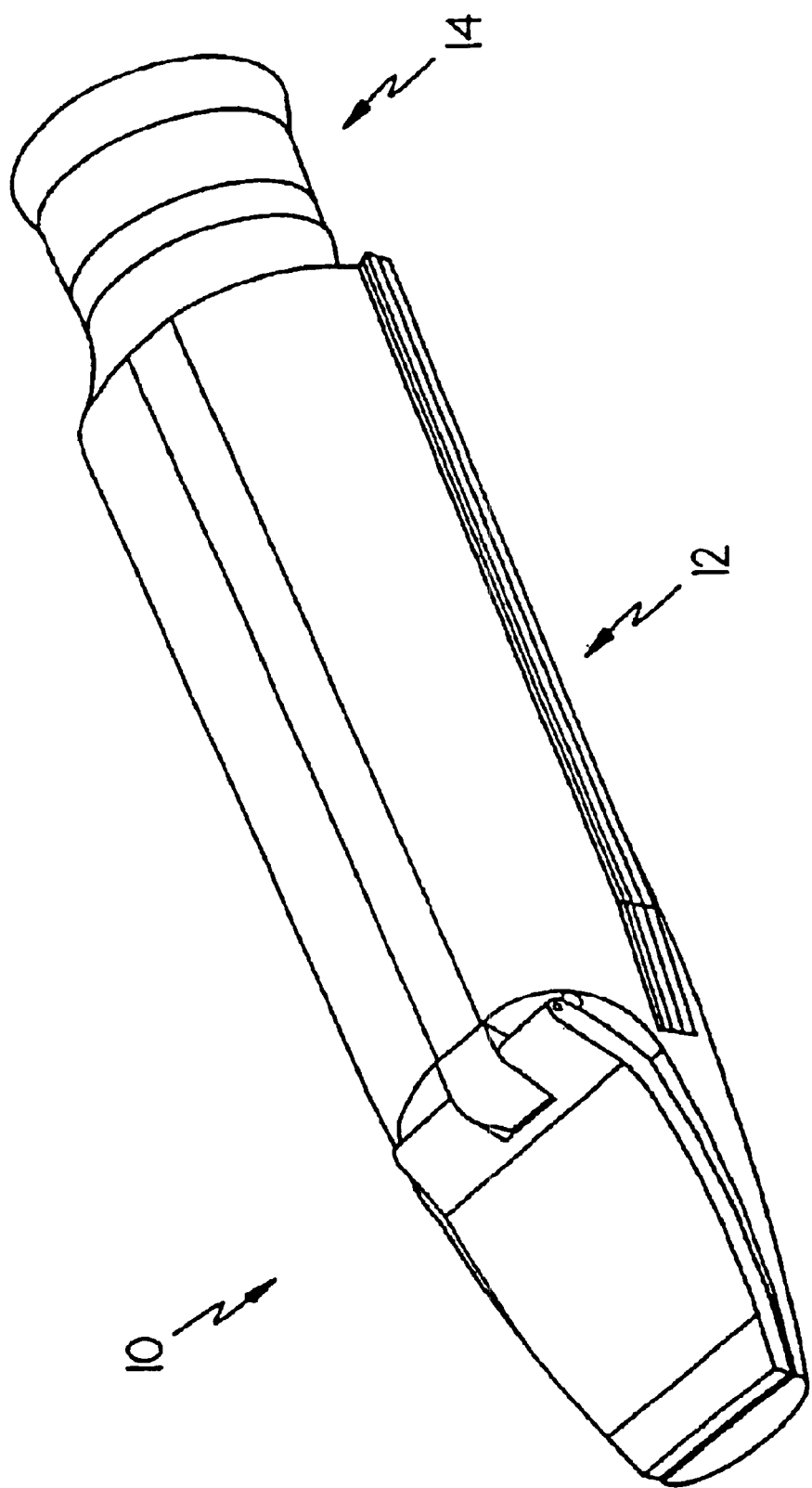
FIG. 10 is a perspective view of the brake fluid refractometer of the present invention.

Turning now to FIG. 10, there is shown a brake fluid refractometer 10 of the present invention comprising a one-piece housing 12 and an output reading device 14. Output reading device 14 can be of any convenient type, such as, for example, a digital output reading device, which allows a user to view the result of a measurement in a digital form. It is contemplated by the present invention that a hydraulic fluid refractometer with a digital output reading device can comprise an array of photosensitive elements for sensing the amount of illumination of the array by incident light.

Figure 11A:
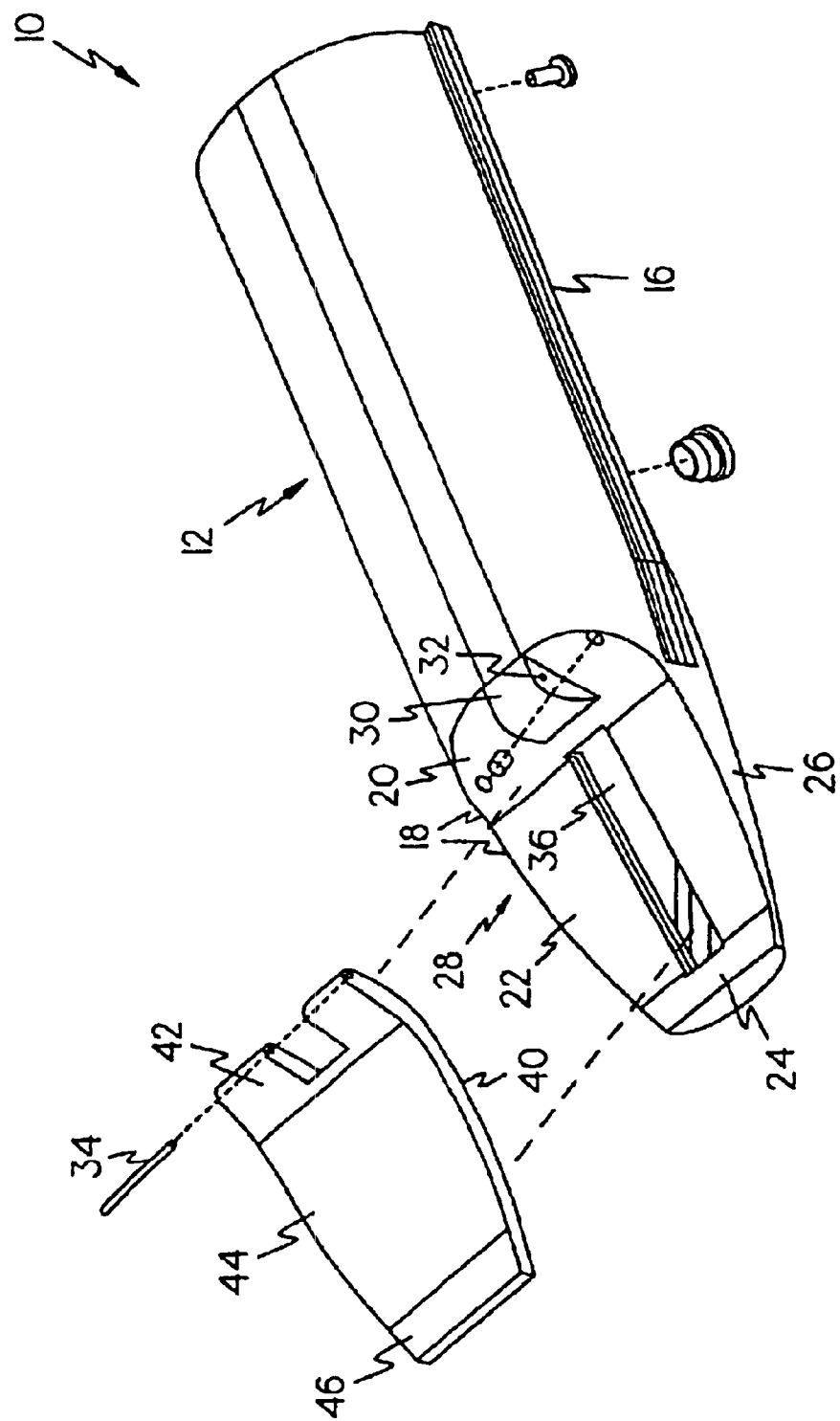
FIG. 11A is an exploded view of a portion of the refractometer of FIG. 10.

As illustrated in FIG. 11A, housing 12 includes an elongated cylindrically shaped handle portion 16 and a reference portion 18 having first and second sloping surfaces 20 and 22, respectively, and a horizontal surface 24 extending and meeting with spaced apart side walls 26 and 28. Sloping surfaces 20 and 22 and spaced apart side walls 26 and 28 join with cylindrically shaped handle portion 16 to form one-piece housing 12 in which optical elements of refractometer 10 are to be disposed.

First sloping surface 20 includes a protrusion 30 having a through bore 32 which is adapted for receiving a hinge means 34. Second sloping surface 22 includes a rectangular opening 36 that allows to deposit a sample fluid on a surface of a critical angle prism 38 (shown in FIG. 12) disposed inside housing 12 and described in detail below. Hinge means 34 in the form of a rod is provided for pivotally connecting cover 40 to protrusion 30 and to allow cover 40 to be in an open position when a sample fluid is being deposited on the critical angle prism, or in a closed position after the sample fluid has been deposited on the critical angle prism. Cover 40 consists of two sloped surfaces 42 and 44 and a third surface 46 which are shaped to cover surfaces 20, 22, and 24 of housing 12 when cover 40 is in the closed position.

Figure 12:
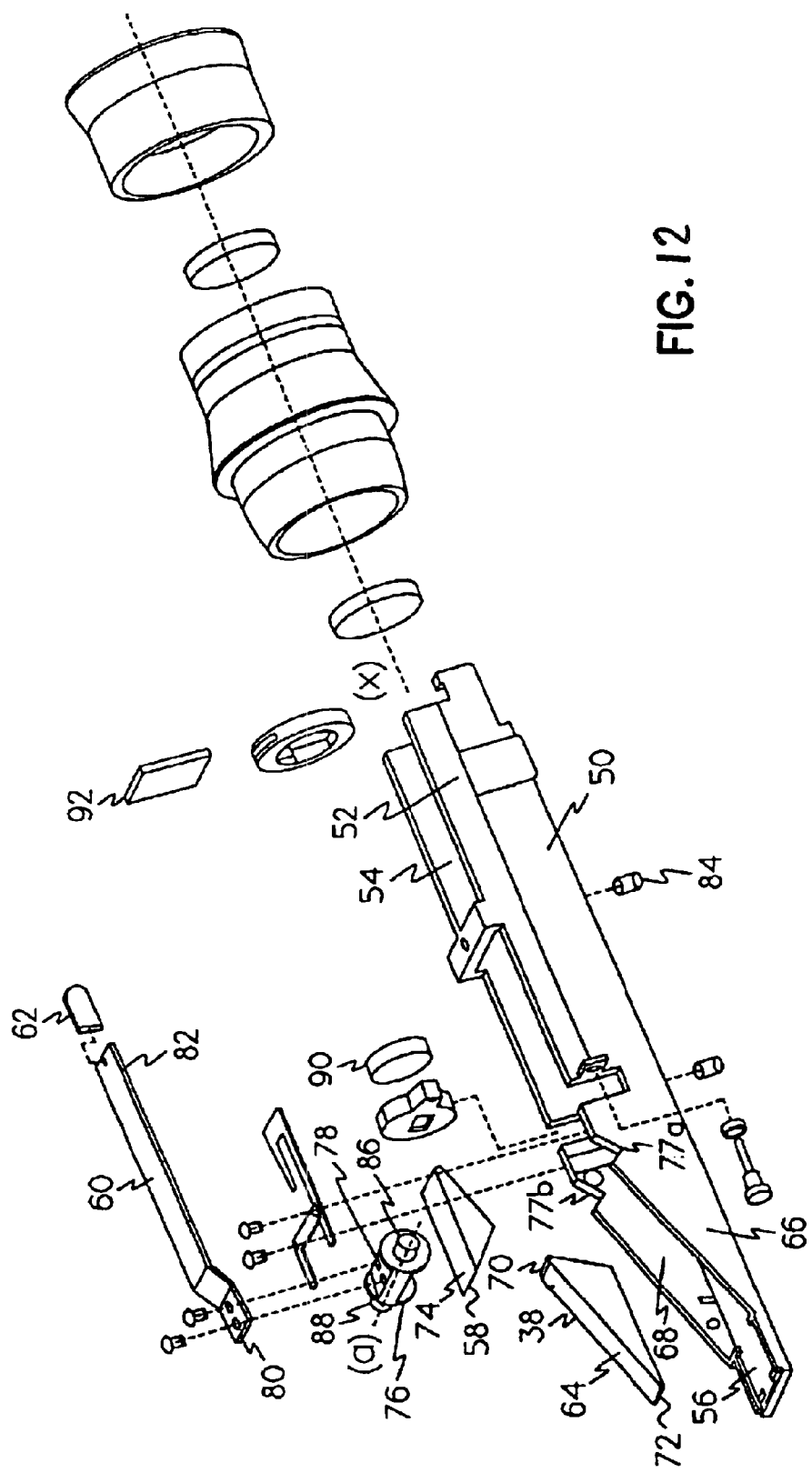
FIG. 12 is an exploded view of components of the refractometer of FIG. 10.

Turning now to FIG. 12, within housing 12 there is located a channel-like frame 50 consisting of two spaced apart side panels 52 and 54 connected to a bottom panel 56. Frame 50 serves as a receptacle for optical elements of the refractometer, comprising critical angle prism 38, a wedge 58, a bimetallic strip 60, and a bimetallic spring means 62. Critical angle prism 38 is disposed within frame 50 between spaced apart side panels 52 and 54 in such a way that a sloping face 64 of critical angle prism 38 is situated in between two sloping ribs 66 and 68 of frame 50 and below second sloping surface 22 of reference portion 18 of housing 12 having rectangular opening 36. A sample fluid is usually deposited on sloping face 64 of critical angle prism 38 through rectangular opening 36. As it is envisioned by the present invention, a sample fluid deposited on sloping face 64 can also comprise sugar solutions, juices, salt solutions, antifreeze, lubrication fluids. Sloping face 64 of critical angle prism 38 meets a second face 70 at one edge of the prism and meets a third face 72 at the opposite edge.

In one embodiment of the present invention, illustrated in FIG. 11A, ambient light illuminates a sample fluid deposited on sloping face 64 and enters an optical path inside the refractometer. In this embodiment cover 40 is made of a clear material which is transparent for ambient light entering the optical path through cover 40.

Figure 11B:
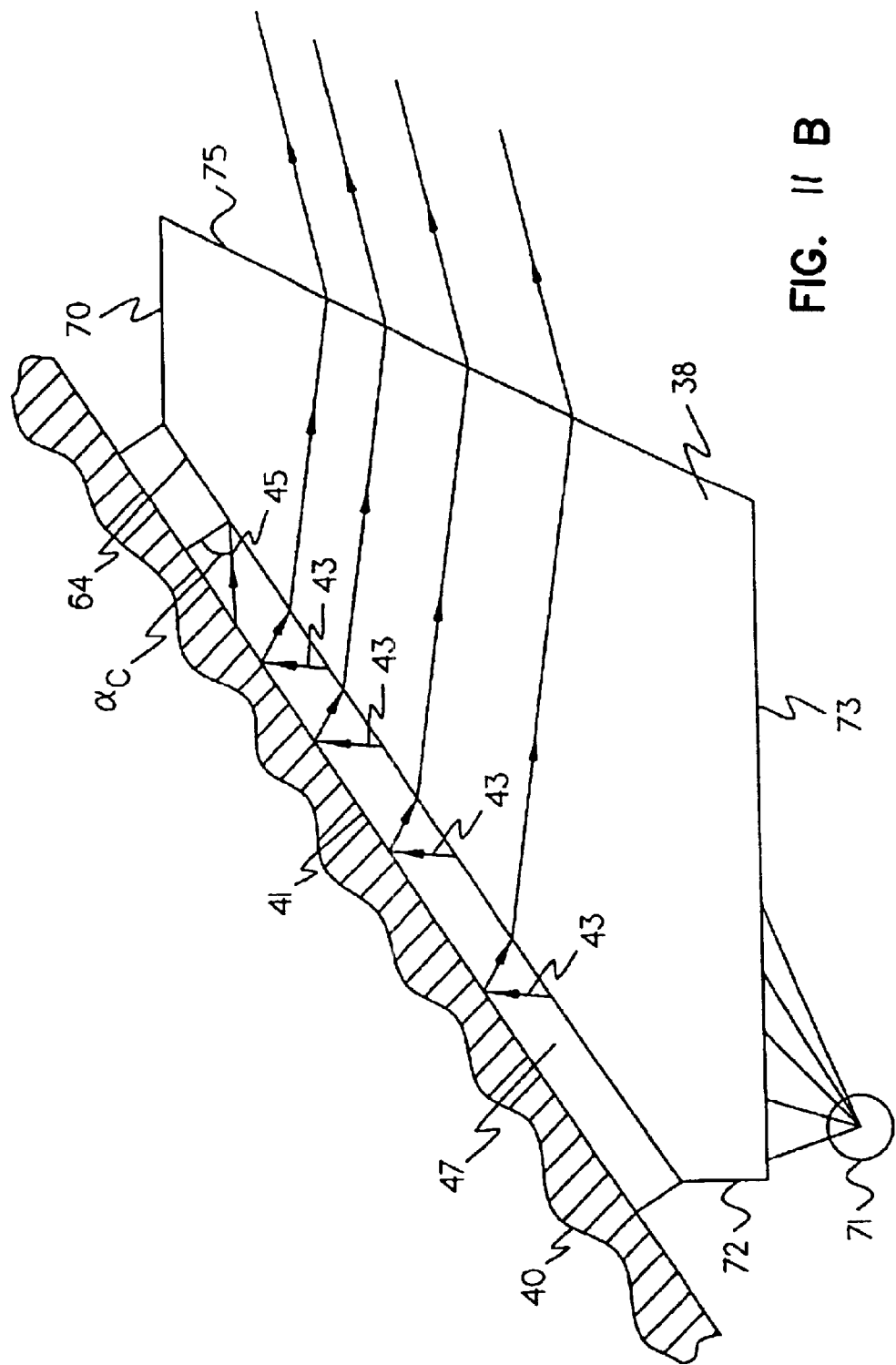
FIG. 11B is a schematic representation of refraction if a critical angle prism illuminated by an LED.

In another embodiment of the present invention, illustrated in FIG. 11B, the light that illuminates a sample fluid 47 on sloping face 64 and enters the optical path is generated by an LED 71 situated under a lower face 73 of critical angle prism 38. The light from LED 71, emitted in all directions, first travels through critical angle prism 38 and through sample fluid 47 until the light reaches a diffuse reflective surface 41 of cover 40. The light from LED 71 is then scattered from diffuse reflective surface 41 in all directions. For example, a plurality of selected parallel beams 43 in FIG. 11B is reflected from diffuse reflective surface 41 back into sample fluid 47, refracts back into critical angle prism 38 at face 64 and exits prism 38 as an array of parallel beams after being refracted once again at a face 75 of prism 38. The light reflected from diffuse reflective surface 41 refracts back into prism 38 at all angles up to the critical angle of refraction. As shown in FIG. 11B, a beam 45 which is incident on face 64 at the critical angle does not enter critical angle prism 38, because it is totally reflected at face 64. All beams which are incident on face 64 at angles greater than the critical angle will not refract back to critical angle prism 38, but will be totally reflected at face 64, therefore, producing a shadowline (not shown) on a reticle. In this embodiment of the present invention it is contemplated that preferably monochromatic LED 71 fits into housing 12 and provides sufficient illumination to form an image on the reticle.

Figure 13:
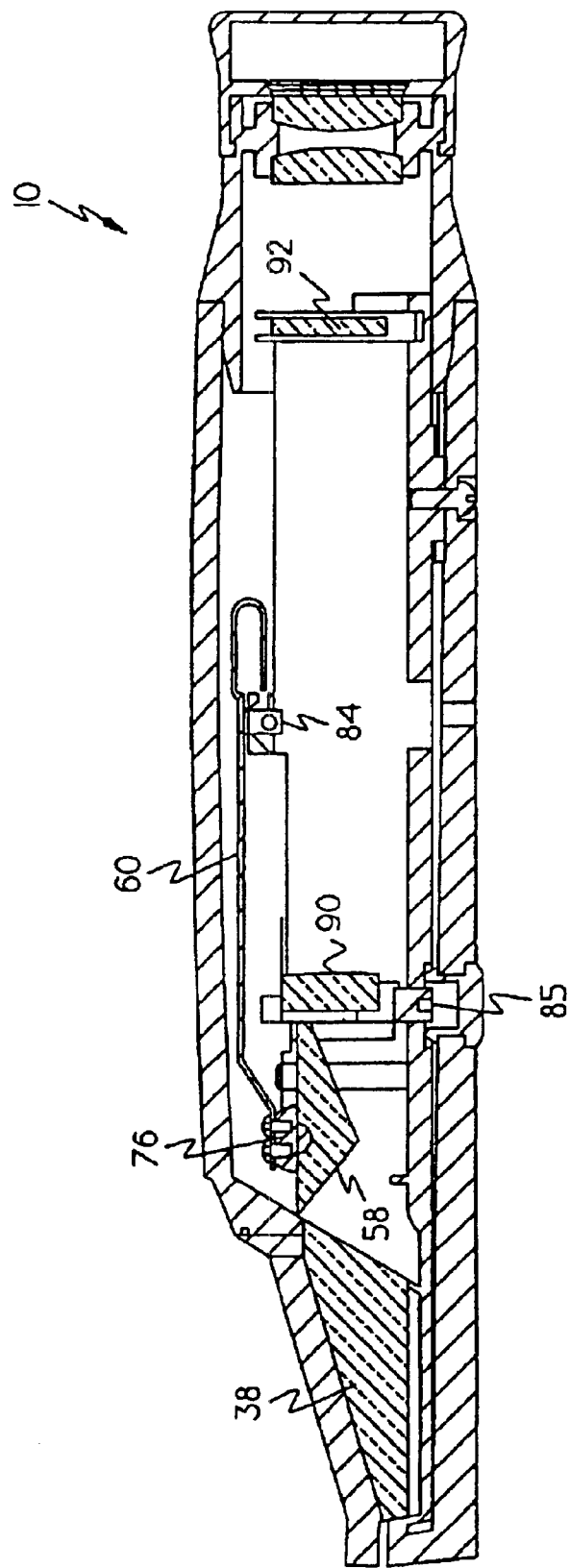
FIG. 13A is a longitudinal sectional view of the refractometer of FIG. 10.
FIG. 13B is a schematic illustration of the calibration procedure.
FIG. 13C is in example of a reticle showing a reading.
FIGS. 13D and 13E illustrate different embodiments of a reticle of the present invention.
FIG. 13F is a side view of a disk-shaped reticle of the present invention.
Figure 13:
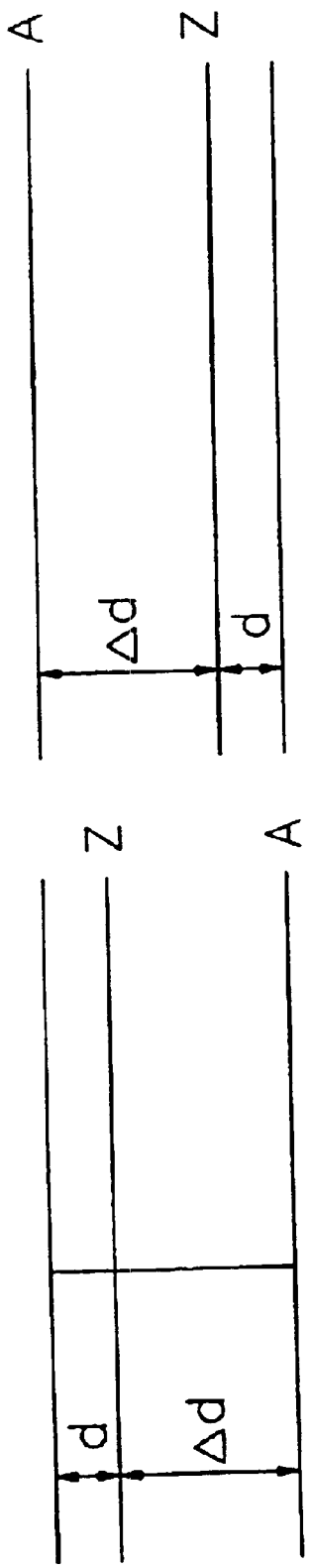
Figure 13:
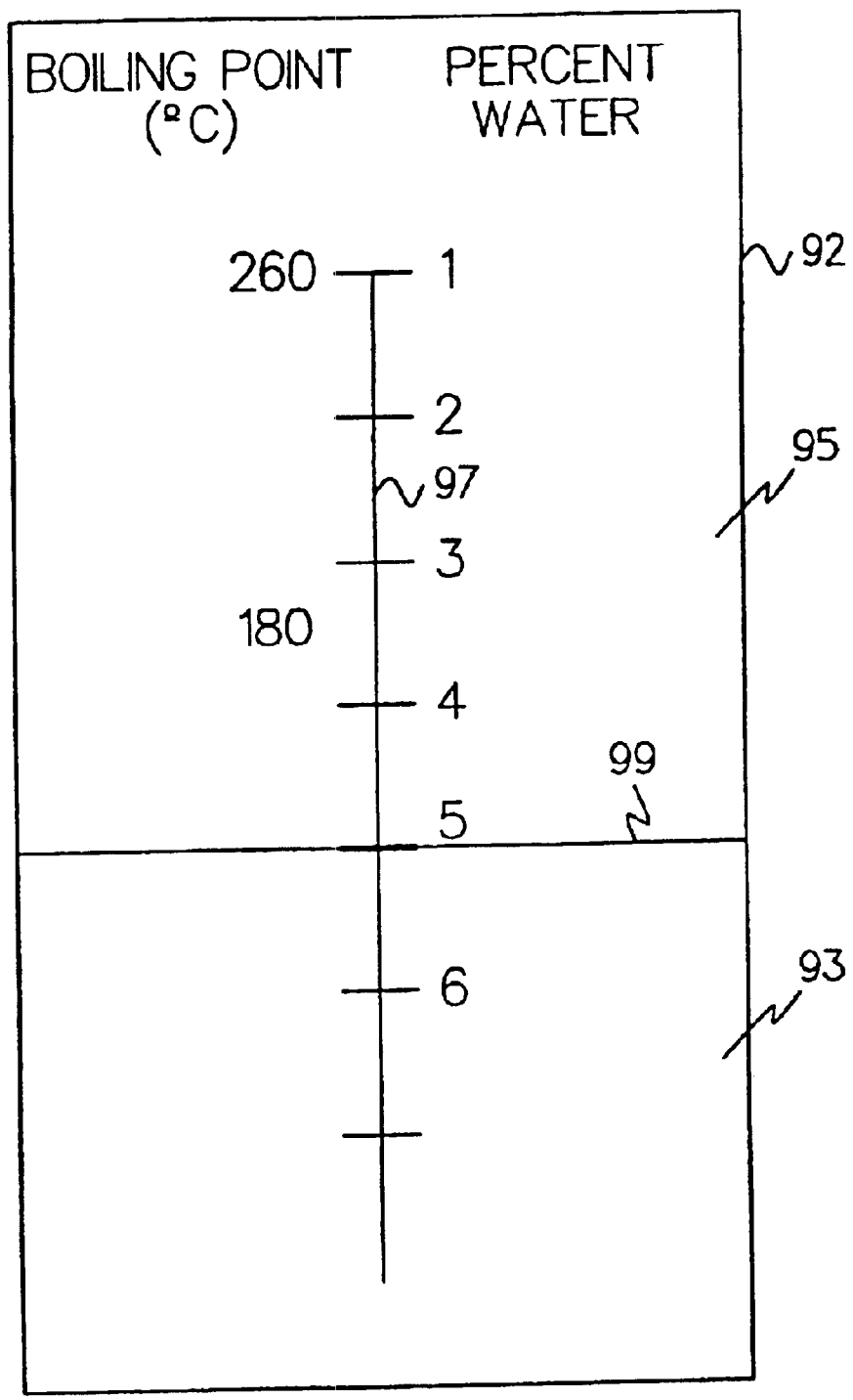
Figure 14:
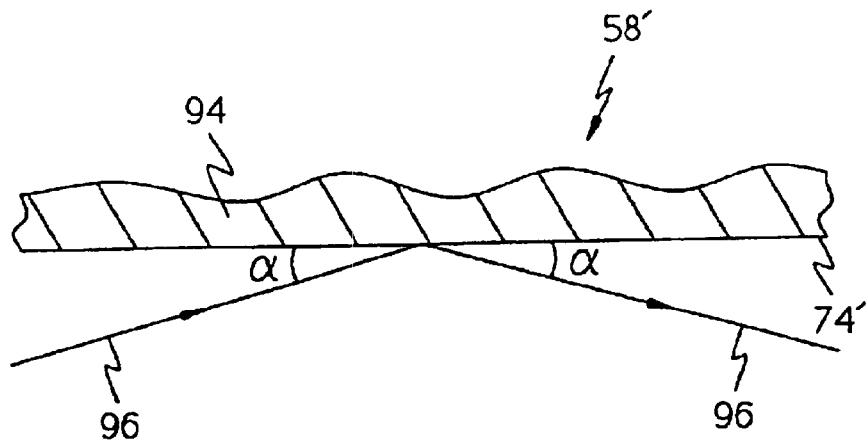
FIGS. 14A and 14B are diagrammatic illustrations of the operation of the one-piece mirror-wedge combination of the present invention.
Figure 14:
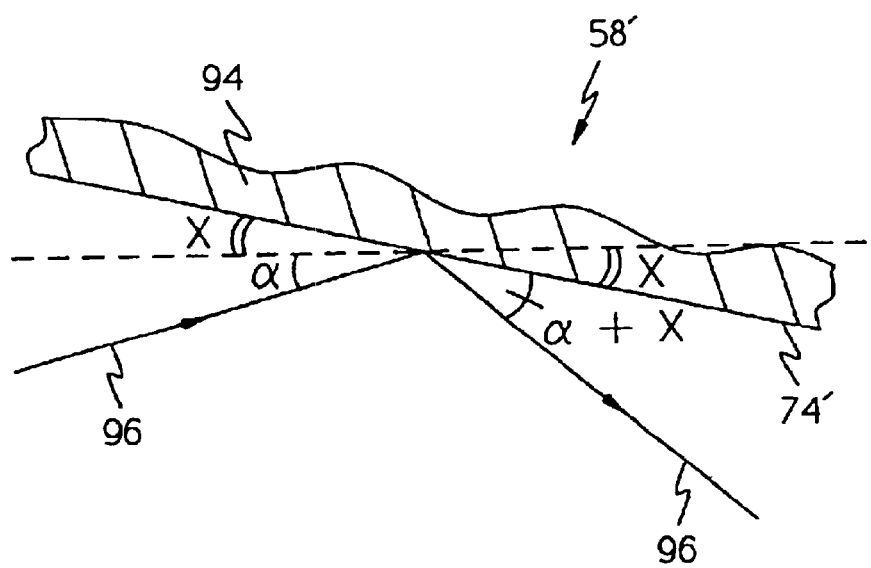

Wedge 58 is mounted inside spaced apart side panels 52 and 54 next to critical angle prism 38, as illustrated in FIGS. 13 and 14A. Major surface 74 of wedge 58 is coated with a reflective coating, thus, transforming major surface 74 into a mirror and transforming wedge 58 into a one-piece mirror-wedge combination. If the refractometer of the present invention is used for a non-hydraulic fluid, then there will be no need to provide reflective coating on wedge 58.

As shown in FIGS. 13 and 14A, the wedge-mirror combination is attached to a pivoting shaft member 76 that is pivotally supported at both ends by spaced apart side panels 52 and 54. In particular, rod-like extensions at opposite axial ends of shaft member 76 seat in notches 77a and 77b in side walls 52 and 54, respectively. Pivoting shaft member 76 has an upper flattened surface 78 and is allowed to rotate about a longitudinal axis (a). A bimetallic strip 60 is attached at its first end 80 to upper flattened surface 78 of pivoting shaft member 76. Bimetallic strip 60 is suspended or cantilevered parallel to the optical axis (x) of the refractometer. The second end 82 of bimetallic strip 60 is secured to a bimetallic spring means 62 which applies a load through bimetallic strip 60 against a set screw 84. Bimetallic strip 60 and spring means 62 together with a one-piece wedge-mirror combination constitute the temperature compensation mechanism utilized in the brake fluid refractometer of the present invention. Temperature changes make bimetallic strip 60 bend and, therefore, drive the wedge-mirror combination in a rotational motion about the axis (a) shown in FIG. 12. When bimetallic strip 60 bends, its has to overcome the friction between ends 86 and 88 of pivoting shaft member 76 and spaced apart side panels 52 and 54 of frame 50. Furthermore, the bimetallic spring 60 /set screw 84 combination exerts the force on bimetallic strip 60 opposite to the direction in which bimetallic strip 60 bends. Therefore, adjusting set screw 84 up and down allows to calibrate the refractometer.

The calibration procedure of the present invention comprises the following steps. First, using a first calibration fluid with a known water content a user observes a position of the boundary between dark and light areas on the reticle as shown by line A in FIG. 13B. If boundary A falls below the reading corresponding to the known water content (line Z in FIG. 13B), an adjustment is made by rotating screw 84 which, in turn, rotates wedge 58, as can be seen in FIG. 13A. Screw 84 is adjusted until boundary A lies above line Z at a distance $d=0.5\times(Z-A)=0.5\times\alpha d$. In the case when the initial measurement produces boundary A above line Z, wedge 58 is adjusted by screw 84 so that boundary a moves to a position below line Z at a distance $d=0.5\times(A-Z)=0.5\times\alpha d$.

The next step of the calibration procedure is to adjust lens 90 by rotating a screw 85 (shown in FIG. 13A) so that boundary A coincides with line Z. Next, using a second calibration fluid the same calibration procedure is repeated. The calibration procedure is repeated until the calibration requirements are met.

After the light passes through a sample fluid deposited on face 64 of critical angle prism 38, one portion of that light gets totally reflected at face 64. The other portion of the light which was not totally reflected then travels through critical angle prism 38, then through wedge 58 and lens 90 to form an image on a reticle 92. As illustrated in FIG. 13C, the image on reticle 92 comprises a dark area 93, corresponding to the totally reflected portion of the light, and a light area 95, corresponding to the light impinging upon reticle 92. Reticle 92 comprises at least one scale 97 with marks corresponding to one or more parameters to be measured, such as, for example, a boiling point or a water content of a hydraulic fluid. A boundary 99 impinges upon reticle 92 at such a mark that corresponds to the measured parameters in a particular hydraulic fluid.

Figure 13D:
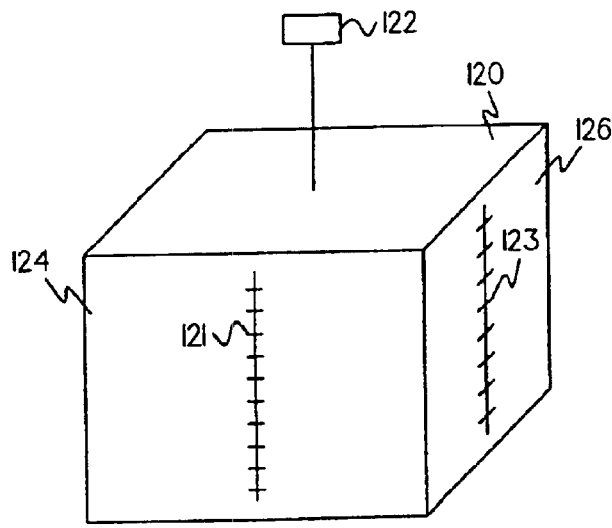

In the refractometer of the present invention it is contemplated that a single apparatus can be used to test different kinds of hydraulic fluids, provided that reticle 92 comprises different scales corresponding to different hydraulic fluids. Such a reticle can be of different shapes and designs. For example, one of the embodiments of the refractometer of the present invention comprises a reticle 120 shaped as a cube or a rectangular prism, as illustrated in FIG. 13D. In this embodiment reticle 120 is rotated in the refractometer by a knob 122. Side faces of reticle 120 comprise scales that correspond to different types of hydraulic fluids. As shown in FIG. 13D, faces 124 and 126 of reticle 120 comprise scales 121 and 123, respectively. A user will see such a face of reticle 120 that coincides with an image plane on which an image is formed. Therefore, the user will be provided with a reading corresponding to a particular type of hydraulic fluid on a scale coinciding with the image plane.

By turning knob 122 a different scale is placed into image plane and, therefore, the same refractometer can be utilized for measuring a boiling point and a water content of a different brake fluid.

Figure 13E:
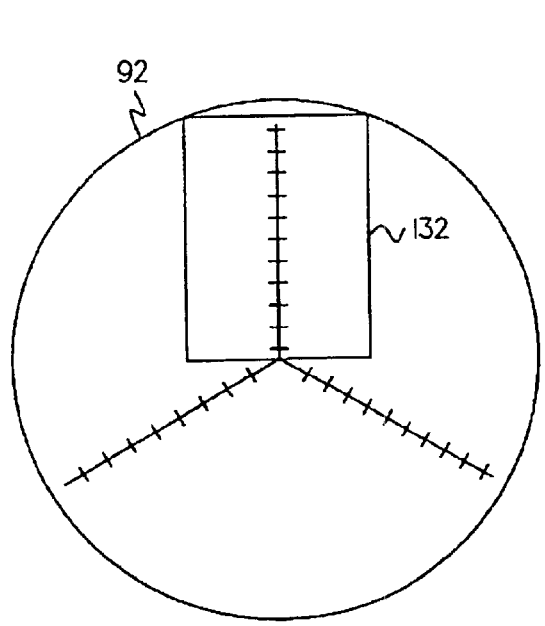
Figure 13:
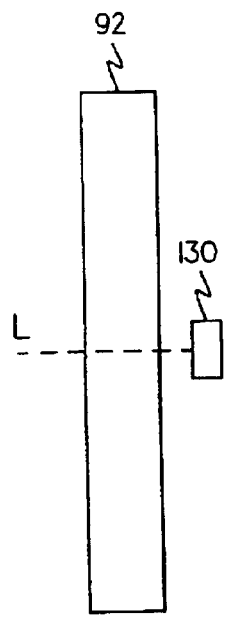

In yet another embodiment of a single refractometer used for testing various hydraulic fluids reticle 92 is disc-shaped, as illustrated in FIGS. 13E and 13F. A number of scales, corresponding to different types of brake fluids, is depicted on the reticle. The reticle can be rotated around axis L by a knob 130. An image area 132 comprises a scale that corresponds to a particular hydraulic fluid and can be viewed by a user. When properties of another brake fluid are measured by the refractometer, reticle 92 is rotated so that the appropriate scale is positioned in image area 132.

In a situation when a refractometer is used only for a certain kind of hydraulic fluid, a user is provided with a kit of several refractometers. Each of the refractometers is manufactured and calibrated for use with a particular hydraulic fluid. The user selects the refractometer corresponding to the type of a fluid that needs be tested.

It is important to emphasize that having temperature compensating means in the form of a one-piece mirror-wedge combination coupled to a bimetallic member provides a novel device for the proper temperature compensation function of the refractometer of the present invention. Coated surface 74 of the wedge-mirror combination increases the angular deviation of the beam of light travelling from the critical angle prism 38 into the wedge 58 in a ratio of 2 to 1. FIGS. 14A and B show diagrammatically wedge 58' having surface 74' provided within reflective coating 94. As illustrated in FIGS. 14A and 14B, when the mirror 58' rotates X degrees, beam 96 deviates 2X degrees from its previous position. If surface 74' of wedge 58 were not coated with a reflective coating and did not work as a mirror, then rotation the wedge by 1 degree would lead to an angular displacement of the beam of only a fraction of 1 degree. Also, a larger angular displacement of the beam solves the problem of stretching a narrower range of brake fluid refractive indices over a larger scale that is normally used in refractometers for coolants, because a larger angular displacement carried over the distance between a focusing lens 90 and reticle 92 provides a larger span of an image on the scale of the reticle.

Figure 15:
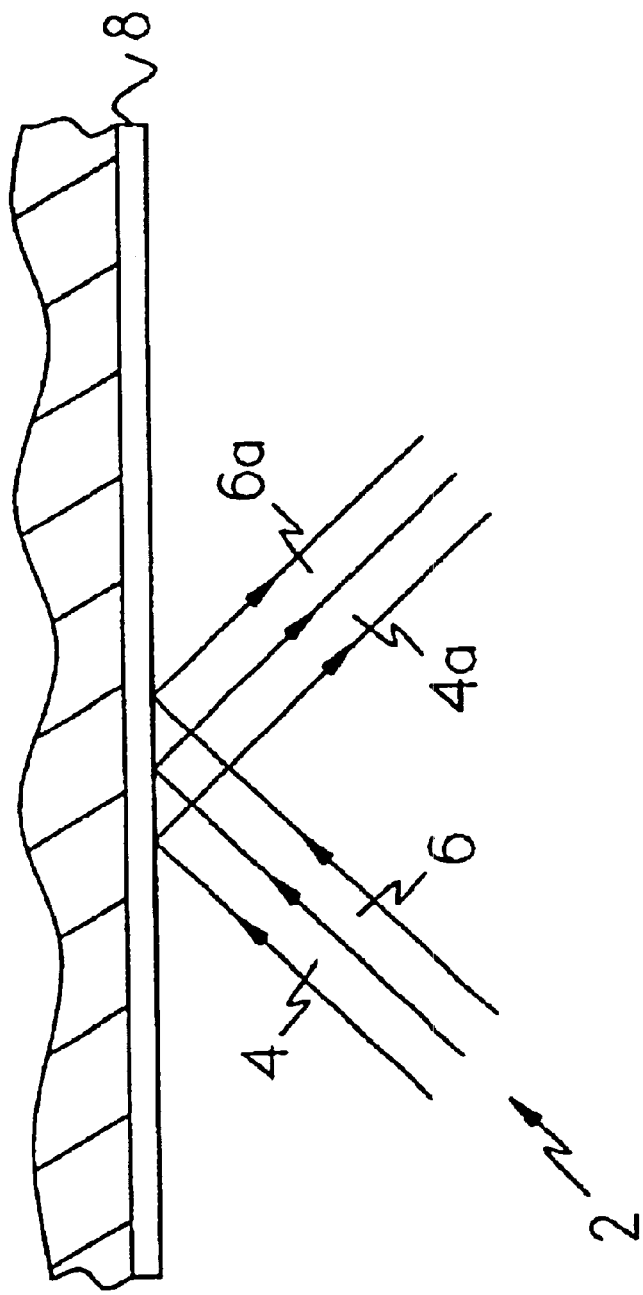
FIG. 15 is a diagrammatic view illustrating the image inversion in the refractometer of the present invention.
Figure 16C:
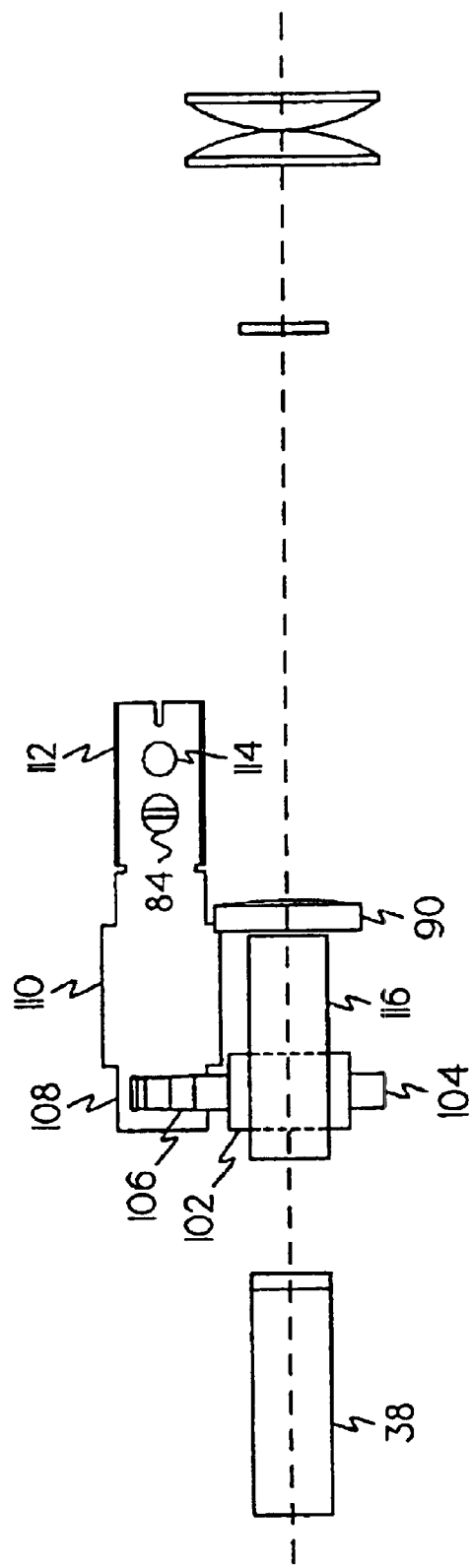
FIGS. 16A–16D are exploded views, partly diagrammatic, illustrating an alternative embodiment of the refractometer of the present invention.
Figure 16:
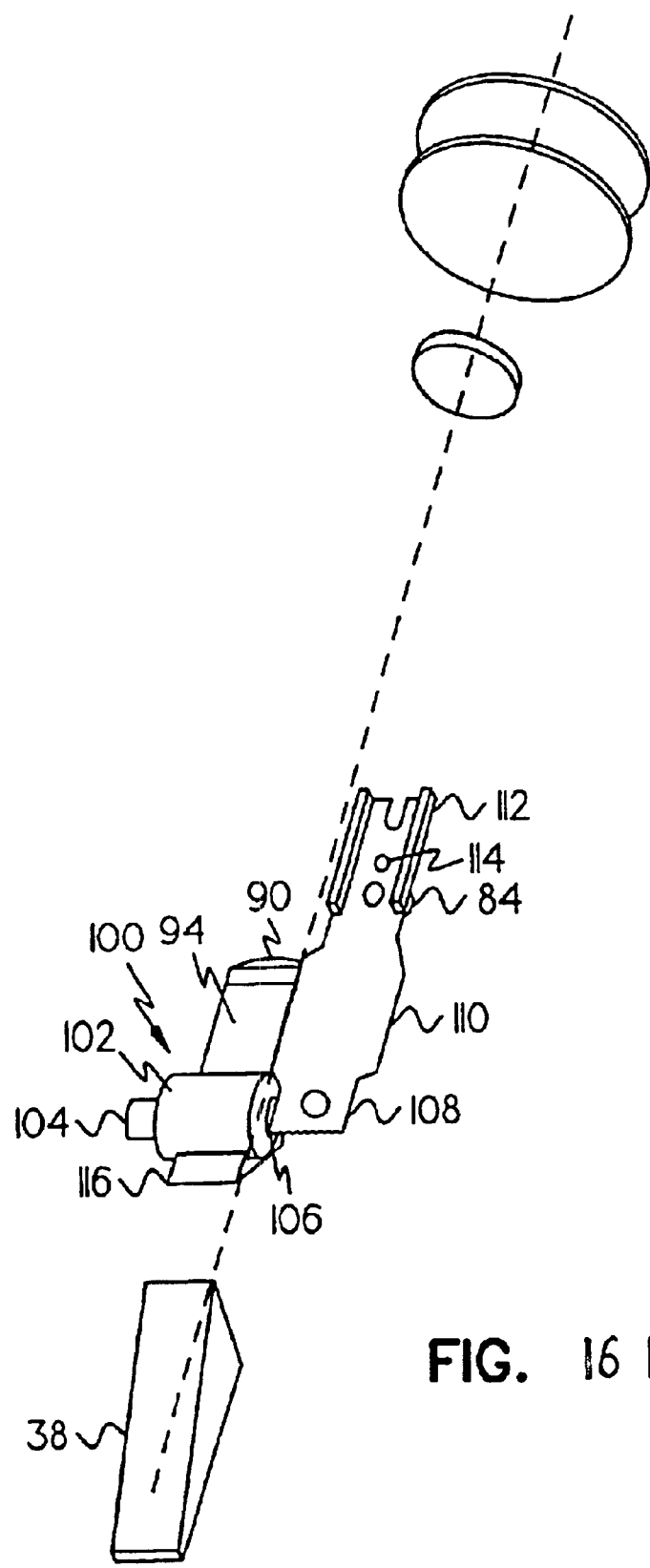

The same mirror serves as an image inverter in the refractometer. As illustrated in FIG. 15, a portion 4 of a beam 2 that previously was totally reflected on the boundary between the sample fluid and the critical angle prism 38 (the upper dark portion) and a portion 6 of beam 2 that was not totally reflected (the lower light portion) change places after beam 2 is reflected by the mirror 8. The upper dark portion 4 becomes the lower dark portion 4a after reflection, the lower light portion 6 becomes the upper light portion 6a, thus, achieving inversion of the image that a user will see on the reticle scale.

An alternate embodiment of the present invention is illustrated in FIGS. 16A–16D. In this embodiment a pivoting shaft member 100 has a cylindrically shaped central portion 102 and two oppositely spaced ends: a first end 106 and a second end 104. One end 108 of a bimetallic strip 110 is attached to a first end 106 of a pivotal shaft member 100. The other end 112 of bimetallic strip 110 is attached to a spring means 114. In this embodiment when bimetallic strip 110 bends due to a change of temperature, it applies a rotational force on first end 106 of pivoting shaft member 100 which causes rotation of a one-piece wedge-mirror combination 116, therefore, providing temperature compensation in the refractometer.

Figure 17:
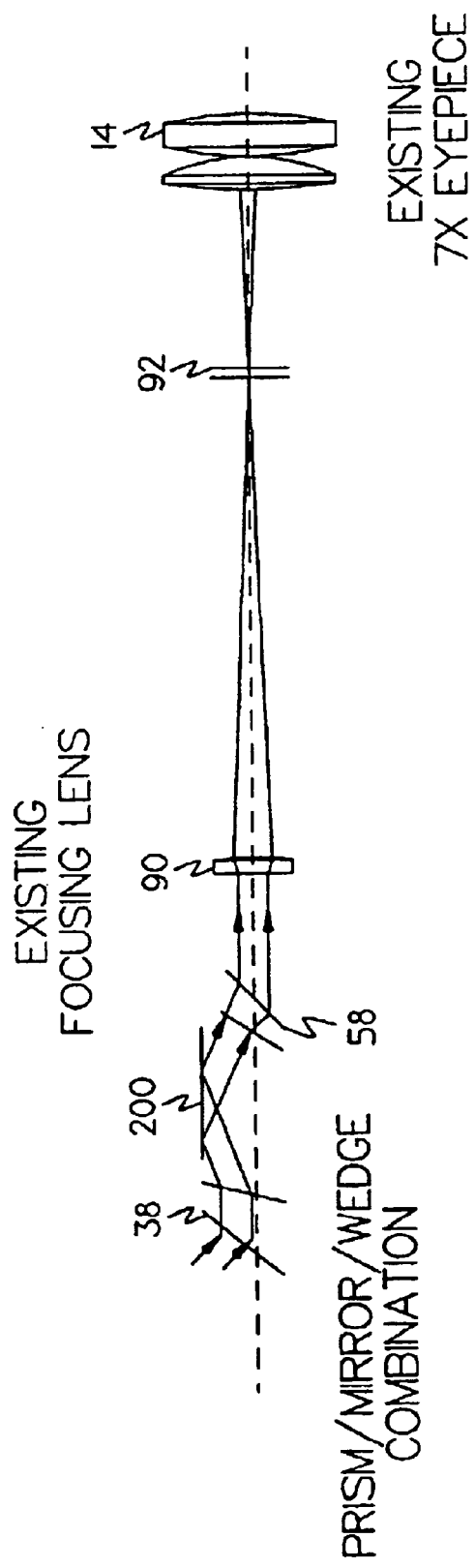
FIGS. 17–19 are diagrammatic views illustrating further embodiments of the brake fluid refractometer of the present invention.
Figure 18:
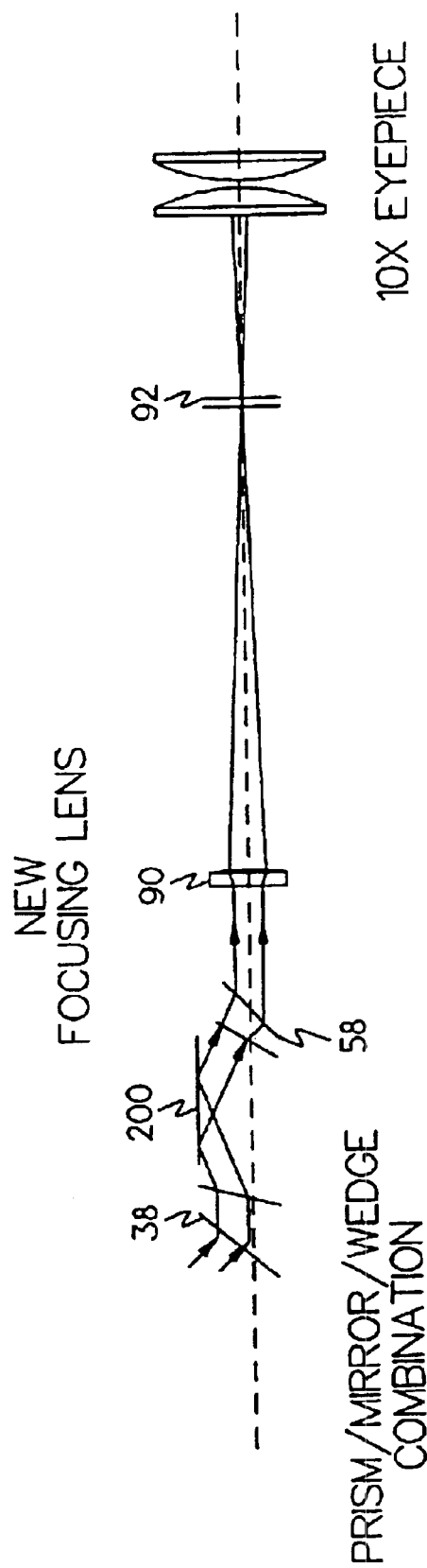
Figure 19:
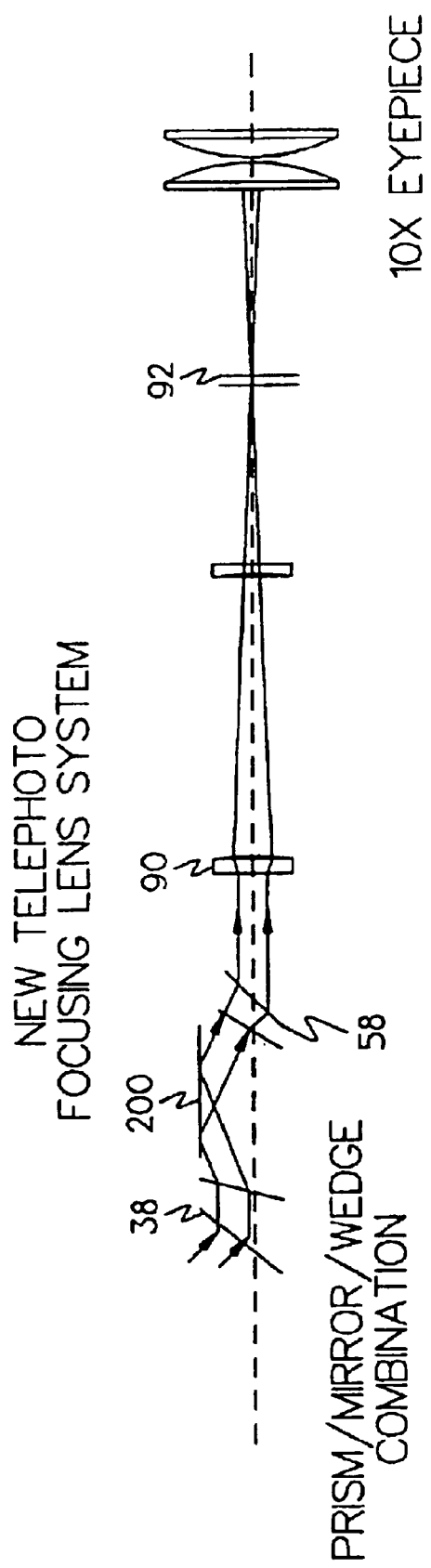

Other embodiments of the brake fluid refractometer of the present invention comprise a mirror 200 and wedge 58 not as a one-piece element, but as two separate optical elements, as illustrated in FIGS. 17 and 18. FIG. 18 shows a three-piece prism 38—wedge 58—mirror 200 combination that magnifies the image 10 times, as opposed to a 7 fold magnification in an optical scheme shown in FIG. 17. FIG. 19 depicts the prism 38—wedge 58—mirror 200 combination with a telephoto focusing lens system. The telephoto focusing lens system is used to focus the image at a shorter distance, because the brake fluid refractometer is manufactured to be housed into a housing of a predetermined sized, such as the housing manufactured for coolant refractometers.

It is also contemplated that the refractometer for hydraulic fluids of the present invention is provided together with the instructions on how to operate the refractometer. In particular, a user will be instructed to deposit a sample of the hydraulic fluid that is being tested on a surface of the critical angle prism.

It is appreciated that various modifications to the inventive concepts described herein may be apparent to those of ordinary skill in the art without departing from the spirit and scope of the present invention as defined by the appended claims.

What is claimed is:

1. A refractometric apparatus for use with fluids comprising:
   means for defining an optical path;
   a reticle located along the optical path, the reticle further comprising markings that increase in the direction of increased water content in a fluid;
   a prism located along the optical path in a spaced relation to the reticle, the prism having a face disposed toward a sample of the fluid, the prism being located to receive light for illuminating the sample of the fluid, whereby a transition between light and darkness is a function of a water content in the fluid;
   a second prism located along the optical path between the prism and the reticle; and
   a temperature sensitive means operatively engaging the second prism for pivotal motion of the second prism in response to temperature changes so as to compensate for temperature changes by altering the optical path in response to such changes;
   whereby the reticle provides a reading relating to the water content of the fluid.

2. The refractometric apparatus of claim 1, wherein the fluid comprises a sugar solution, a juice, a salt solution, an antifreeze, or a lubricant.

3. The refractometric apparatus of claim 1, further comprising focusing means for forming an image on the reticle, the focusing means being disposed along the optical path between the second prism and the reticle.

4. The refractometric apparatus of claim 1, further comprising a frame, wherein the temperature sensitive means is pivotally coupled to the frame and further mechanically coupled to the second prism, the temperature sensitive means further comprising a bimetal strip and a bimetal spring.

5. The refractometric apparatus of claim 4, wherein the fluid comprises a sugar solution, a juice, a salt solution, an antifreeze, or a lubricant.

6. A refractometric apparatus for use with a fluid comprising:

means for defining an optical path;

an array of photosensitive elements located along the optical path, the array being electrically coupled to a character display;

a prism located along the optical path in spaced relation to the array of photosensitive elements, the prism having a face disposed toward a sample of the fluid, the prism being located to receive light for illuminating the sample of the fluid, whereby a transition between light and darkness is a function of a water content in the fluid;

a second prism located along the optical path between the prism and the array of photosensitive elements; and a temperature sensitive means operatively engaged with the second prism for pivotal motion of the second prism in response to temperature changes so as to compensate for temperature changes by altering the optical path in response to such changes;

whereby the character display provides a reading relating to the water content of the fluid.

7. The refractometric apparatus of claim 6, further comprising a frame, wherein the temperature sensitive means is pivotally coupled to the frame and further mechanically coupled to the second prism, the temperature sensitive means further comprising a bimetal strip and bimetal spring.

8. The refractometric apparatus of claim 7, wherein the fluid comprises a sugar solution, a juice, a salt solution, an antifreeze, or a lubricant.

9. The refractometric apparatus of claim 6, wherein the fluid comprises a sugar solution, a juice, a salt solution, an antifreeze, or a lubricant.

10. A method for measuring water content in a fluid for use with an apparatus comprising means for defining an optical path, a critical angle prism, the critical angle prism having a face, a temperature compensation means, and a reticle disposed along the optical path, the method comprising:

placing the fluid on the face of the critical angle prism;

allowing light to enter the optical path through the fluid;

compensating for temperature changes by altering the optical path in response to the ambient temperature; and observing a boundary between light and darkness on the reticle to measure water content of the fluid.

11. The method of claim 10, wherein the fluid comprises a sugar solution, a juice, a salt solution, an antifreeze, or a lubricant.

12. A method for measuring water content in a fluid for use with an apparatus comprising means for defining an optical path, a critical angle prism, the critical angle prism having a face, a temperature compensation means, and an array of photosensitive elements disposed along the optical path and electrically couples to a character display, the method comprising:

placing the fluid on the face of the critical angle prism;

allowing light to enter the optical path through the fluid;

compensating for temperature changes by altering the optical path in response to the ambient temperature; and observing a reading on the character display, the reading being indicative of a water content of the fluid.

13. The method of claim 12, wherein placing the fluid comprises placing a sugar solution, a juice, a salt solution, an antifreeze, or a lubricant.

14. In a method of measuring water content in a fluid for use with an apparatus comprising means for defining an optical path, a critical angle prism, the critical angle prism having a face, a temperature compensation means, and a reticle disposed along the optical path, a calibration method comprising:

placing the fluid on the face of the critical angle prism, the fluid being of a known water content;

allowing light to pass through the fluid and to enter the optical path; and adjusting the optical path so that a boundary between light and darkness on the reticle impinges upon the reticle at a predetermined point.

15. The method of claim 14, wherein the fluid comprises a sugar solution, a juice, a salt solution, an antifreeze, or a lubricant.

16. In a method of measuring water content in a fluid for use with an apparatus comprising means for defining an optical path, a critical angle prism, the critical angle prism having a face, a temperature compensation means, and an array of photosensitive elements electrically coupled to a character display and disposed along the optical path, a calibration method comprising the steps of:

placing the fluid on the face of the critical angle prism, the fluid being of a known water content;

allowing light to pass through the fluid and enter the optical path; and adjusting the optical path so that a boundary between the light and darkness impinges upon the array of photosensitive element at a predetermined point, producing a predetermined reading on the character display.

17. The method of claim 16, wherein the fluid comprises a sugar solution, a juice, a salt solution, an antifreeze, or a lubricant.

* * * * *